US012807651B2

(12) United States Patent
Hool

(10) Patent No.: US 12,807,651 B2
(45) Date of Patent: Nov. 24, 2026

(54) PEPTIDES FOR USE IN THE TREATMENT OR PREVENTION OF MYOCARDIAL DAMAGE

(71) Applicant: THE UNIVERSITY OF WESTERN AUSTRALIA, Nedlands (AU)

(72) Inventor: Livia Hool, Nedlands (AU)

(73) Assignee: THE UNIVERSITY OF WESTERN AUSTRALIA, Nedlands (AU)

( * ) Notice: Subject to any disclaimer, the term of this patent is extended or adjusted under 35 U.S.C. 154(b) by 801 days.

(21) Appl. No.: 18/043,880

(22) PCT Filed: Aug. 20, 2021

(86) PCT No.: PCT/AU2021/050928

§ 371 (c)(1),
(2) Date: Mar. 2, 2023

(87) PCT Pub. No.: WO2022/036411

PCT Pub. Date: Feb. 24, 2022

(65) Prior Publication Data

US 2024/0158447 A1 May 16, 2024

(30) Foreign Application Priority Data

Aug. 21, 2020 (AU) ................................ 2020902986

(51) Int. Cl.

| | |
|---|---|
| ***C07K 14/00*** | (2006.01) |
| ***A61P 9/04*** | (2006.01) |
| ***C07K 7/08*** | (2006.01) |
| *A61K 38/00* | (2006.01) |

(52) U.S. Cl.

CPC .............. *C07K 14/001* (2013.01); *A61P 9/04* (2018.01); *C07K 7/08* (2013.01); *A61K 38/00* (2013.01)

(58) Field of Classification Search

CPC ...... A61P 9/00; A61P 9/04; A61P 9/10; A61K 38/00; C07K 14/705

See application file for complete search history.

(56) References Cited

U.S. PATENT DOCUMENTS

| | | | |
|---|---|---|---|
| 2005/0288489 | A1 | 12/2005 | Hirsch |
| 2015/0250854 | A1 | 9/2015 | Beguin et al. |
| 2019/0250145 | A1 | 8/2019 | Marx et al. |

FOREIGN PATENT DOCUMENTS

| | | | |
|---|---|---|---|
| WO | 2013113060 | A1 | 8/2013 |

*Primary Examiner* — Gyan Chandra

(74) *Attorney, Agent, or Firm* — SZDC Law PC

(57) ABSTRACT

The present invention relates to peptides which bind the L-type $Ca^{2+}$ channel. The present invention also relates to methods to treat, prevent or ameliorate the effects of myocardial damage. The present invention also relates to pharmaceutical compositions comprising said peptides.

6 Claims, 36 Drawing Sheets

Specification includes a Sequence Listing.

Figure 3(a)
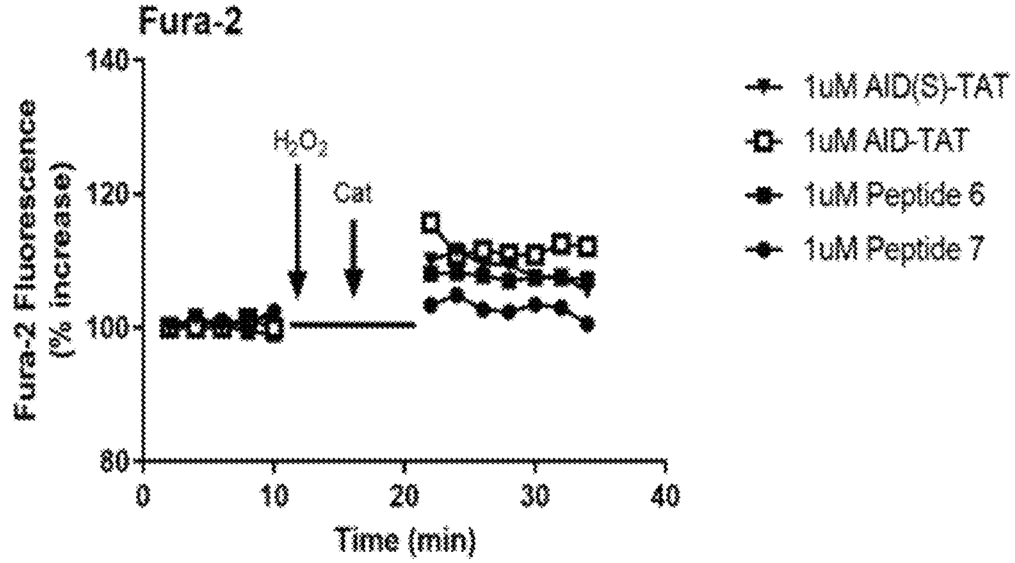
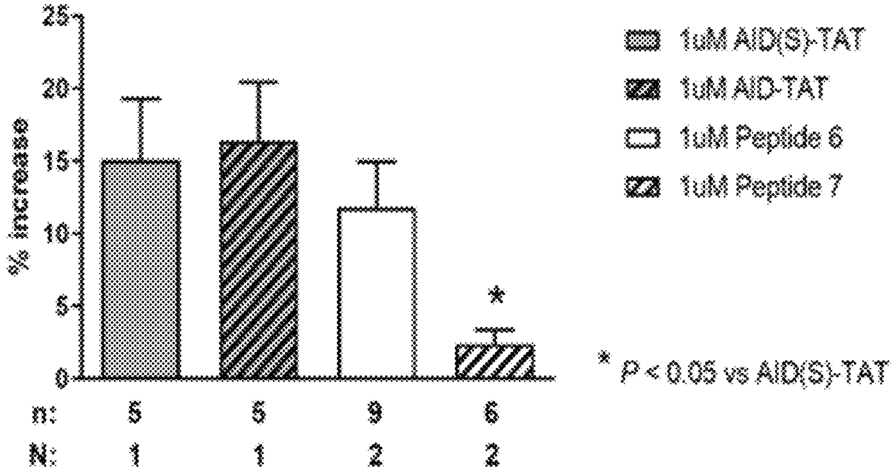

Figure 3(b)
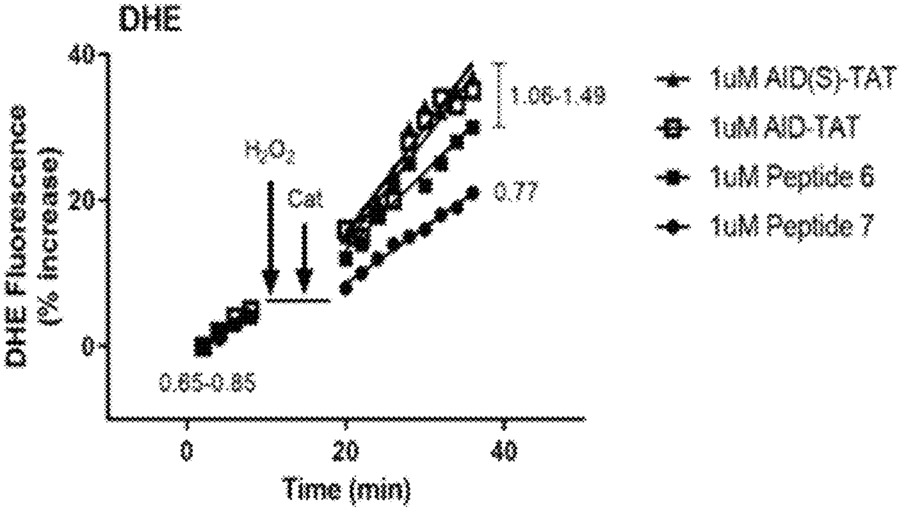
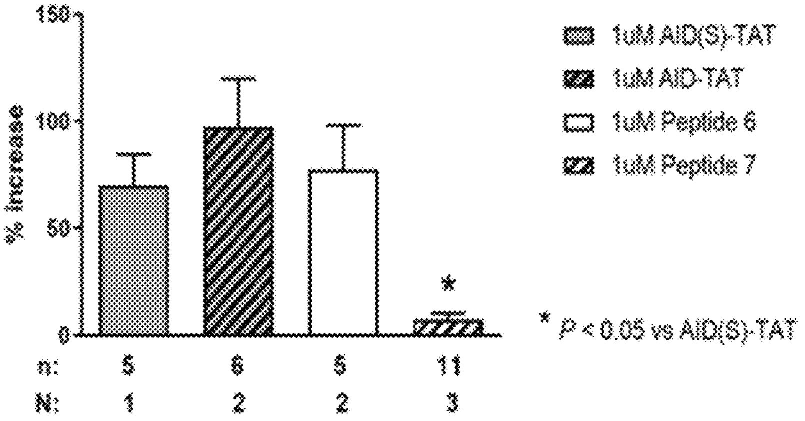

Figure 3(c)
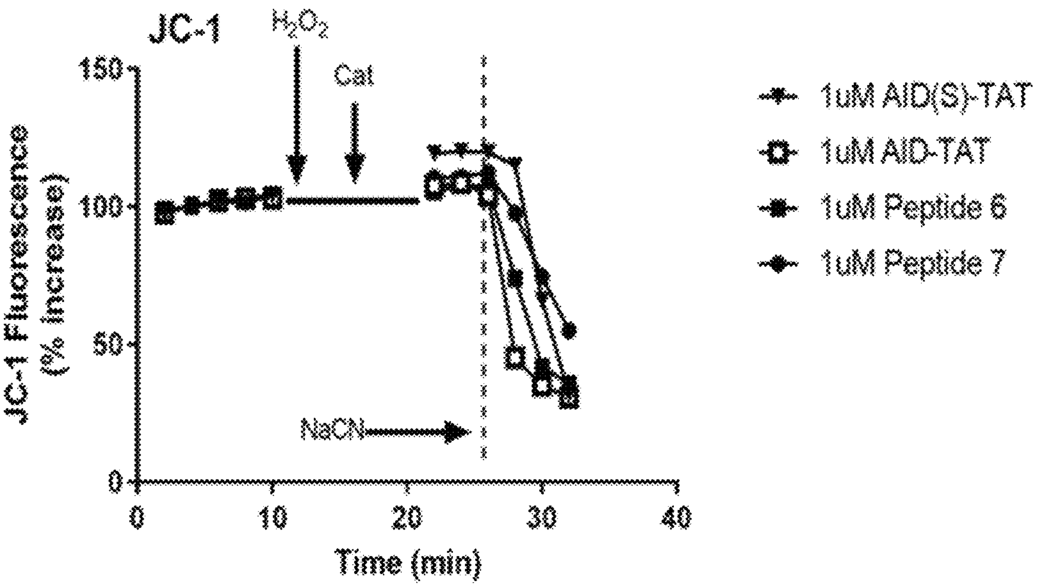
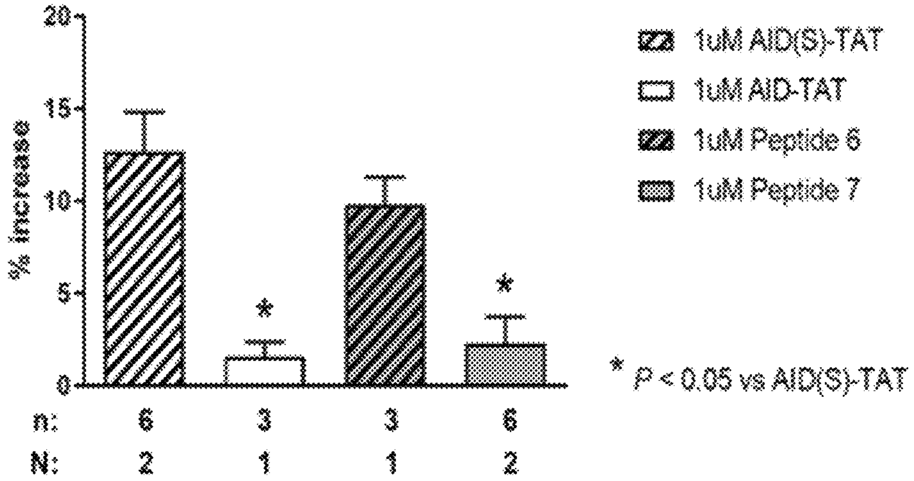

Figure 7

Sequence IDs

| SEQ ID NO | Sequence | Description |
|---|---|---|
| SEQ ID NO: 1 | QQLEEDLKGYLDWITQAE | AID Peptide |
| SEQ ID NO: 2 | $QQX_1EEDX_2KGYLDWITQAE$ | Variant AID Peptide of the invention |
| SEQ ID NO: 3 | RKKRRQRRRZaa | TAT Peptide |
| SEQ ID NO: 4 | QQQEEDLKGYLDWITQAE | Variant P7 |
| SEQ ID NO: 5 | QQEEEDLKGYLDWITQAE | Variant P14 |
| SEQ ID NO: 6 | QQEEEDEKGYLDWITQAE | Variant P15 |
| SEQ ID NO: 7 | QQREEDLKGYLDWITQAE | Variant P16 |
| SEQ ID NO: 8 | GRKKR | Nuclear localisation signal of TAT |
| SEQ ID NO: 9 | YGRKKRRQRRR | Protein transduction domain of TAT |
| SEQ ID NO: 10 | QKILGEWDLAQYTDQELE | AID scrambled peptide |
| SEQ ID NO: 11 | DLKGYLDWITQAE | Variant P1 |
| SEQ ID NO: 12 | LEEDLKGYLDWITQAE | Variant P4 |
| SEQ ID NO: 13 | KGYLDWITQAE | Variant P6 |
| SEQ ID NO: 14 | DLKGYLDWITQA | Variant P10 |
| SEQ ID NO: 15 | DLKGYLDWITQ | Variant P11 |
| SEQ ID NO: 16 | DLKGYLDWIT | Variant P12 |
| SEQ ID NO: 17 | QQLEEDLKGFLDAATQAE | Variant P13 |

Figure 8

Echocardiographic parameters of cTnI-G203S mice administered 10 μM AID(S)-TAT or AID-TAT.

| LVEDD (mm) | LVESD (mm) | FS (%) | LVDPW (mm) | LVSPW (mm) | IVDS (mm) | IVSS (mm) | HW:BW (mg/g) | HR (bpm) |
|---|---|---|---|---|---|---|---|---|
| ***PRE HCM TREATMENT (from 20 weeks)*** | | | | | | | | |
| **25 week old *wt*, AID(S)-TAT (n=4)** | | | | | | | | |
| 3.56 ± 0.12 | 2.31 ± 0.06 | 35.08 ± 1.11 | 1.26 ± 0.08 | 1.42 ± 0.05 | 0.76 ± 0.01 | 0.86 ± 0.01 | 4.33 ± 0.07 | 450 ± 37 |
| **25 week old *cTnI-G203S*, AID(S)-TAT (n=7)** | | | | | | | | |
| 3.08* ± 0.06 | 1.62* ± 0.05 | 47.39* ± 0.81 | 1.31 ± 0.03 | 1.43 ± 0.04 | 0.85* ± 0.01 | 0.96* ± 0.02 | 5.14* ± 0.10 | 450 ± 22 |
| **25 week old *cTnI-G203S*, AID-TAT (n=6)** | | | | | | | | |
| 3.33† ± 0.06 | 2.06† ± 0.08 | 38.26† ± 1.61 | 1.23 ± 0.03 | 1.37 ± 0.03 | 0.73† ± 0.00 | 0.82† ± 0.01 | 4.70† ± 0.17 | 452 ± 26 |
| ***POST HCM TREATMENT (from 30 weeks)*** | | | | | | | | |
| **35 week old *cTnI-G203S*, AID-TAT (n=5)** | | | | | | | | |
| 3.18 ± 0.07 | 1.67 ± 0.05 | 48.48 ± 1.07 | 1.26 ± 0.03 | 1.43 ± 0.06 | 0.95 ± 0.03 | 1.05 ± 0.02 | 5.81 ± 0.21 | 450 ± 19 |

LVEDD, left ventricular end diastolic diameter; LVESD, left ventricular end systolic diameter; FS, fractional shortening; LVDPW, left ventricular posterior wall in diastole; LVSPW, left ventricular posterior wall in systole; IVDS, intraventricular septum in diastole; IVSS, intraventricular septum in systole. Values reported as mean ± SEM; *$P < 0.05$ compared to *wt* AID(S)-TAT, †$P < 0.05$ compared with *cTnI-G203S* AID(S)-TAT as determined by Kruskal-Wallis tests

PEPTIDES FOR USE IN THE TREATMENT OR PREVENTION OF MYOCARDIAL DAMAGE

This application is the National Stage Application of PCT/AU2021/050928, filed on Aug. 20, 2021, which claims priority to Australian Patent Application No. 2020902986, filed on Aug. 21, 2020, which is incorporated by reference for all purposes as if fully set forth herein.

TECHNICAL FIELD

The present invention relates to peptides which bind the L-type $Ca^{2+}$ channel and use thereof to prevent and treat myocardial damage, including cardiac hypertrophy. The invention provides methods to treat, prevent or ameliorate the effects of myocardial damage, by administration of peptides and therapeutic compositions comprising peptides.

BACKGROUND ART

The following discussion of the background art is intended to facilitate an understanding of the present invention only. The discussion is not an acknowledgement or admission that any of the material referred to is or was part of the common general knowledge as at the priority date of the application.

Pathological cardiac hypertrophy (thickening of the heart muscle) may arise in a human or another animal as a response to stress; disease such as hypertension; heart muscle injury including myocardial infarction; neurohormones; or pollution causing hypoxia due to atmospheric carbon monoxide.

Familial hypertrophic cardiomyopathy (HCM) is an inherited heart condition characterised by cardiac hypertrophy that affects an estimated 1 in 200 people worldwide (*J. Am. Coll. Cardiol.* 65 (12) (2015) 1249-1254). It is the leading cause of sudden cardiac death in people under 40 years of age. Drug therapy and surgical interventions such as septal myectomy are used to manage symptoms in patients suffering from HCM.

Certain genetic mutations are associated with the development of HCM. Cardiac troponin (cTn) is a sarcomeric protein complex that consists of three subunits (cTnT, cTnI and cTnC), and plays a critical role in regulating cardiac contraction and relaxation. The entire cTn complex is anchored to tropomyosin via TnT. TnI regulates contraction in response to changes in intracellular calcium. During the relaxed state, TnI inhibits actin-myosin interaction. When calcium binds to TnC, TnI undergoes a conformational change that allows actin-myosin interaction, and as a result, contraction.

Mutations in the cTnI gene TNNI3 account for approximately 3-5% of genotyped families with HCM. Human HCM causing cTnI mutation Gly203Ser is characterized by apical and ventricular hypertrophy, and in some cases supraventricular and ventricular arrhythmias. In addition, HCM is characterized by myocyte remodelling, myofibril disarray and altered energy metabolism. Mutations in the MYH7 gene, specifically the alphaMHCArg403Ser mutation, is also known to account for approximately 40% of HCM cases.

Drug therapy used to manage the symptoms of people with HCM may include calcium channel antagonists, β-blockers, calcium channel blockers, amiodarone (Pacerone) or disopyramide (Norpace). Diltiazem, a calcium channel blocker, is used to treat symptoms of HCM such as angina, and heart arrhythmias. However, these drugs can cause negative inotropic (contractile) effects and a decrease in blood pressure leading to heart failure.

Antiarrhythmic drug therapy includes amiodarone, disopyramide, angiotensin receptor blockers, propafenone, angiotensin-converting enzyme (ACE) inhibitors and perhexilline. These drugs are ineffective in the prevention of arrhythmias. While surgical insertion of an implantable cardioverter defibrillator therapy can prevent sudden death, the socioeconomic and psychological cost to the patient is substantial.

While these treatments can assist in managing the symptoms of cardiac hypertrophy and HCM, no pharmacological treatment currently exists that can reverse or prevent the development of cardiac hypertrophy in patients.

Cardiac hypertrophy also presents in patients that do not suffer from HCM. Patients that present with cardiac hypertrophy as a result of complete or partial occlusion of a coronary artery are commonly treated with reperfusion therapy, for example using thrombolytic therapy, percutaneous coronary intervention (PCI), or bypass surgery. However, following reperfusion therapy, when blood supply returns to cardiac tissue after a period of ischemia, reperfusion injury can result. The absence of nutrients and oxygen from blood during the period of ischemia causes a condition in which restoration of circulation results in inflammation and oxidative damage. This occurs as a result of the increase in oxidative stress rather than restoration of normal function.

L-Type Calcium Channels

The long- or L-type $Ca^{2+}$ channel is the main route for calcium influx into cardiac myocytes producing the invaluable muscle contraction for the pumping heart. Increases in intracellular calcium and oxidative stress are involved in the pathophysiology of cardiac hypertrophy with increased influx through the L-type $Ca^{2+}$ channel or over-expression of the alpha subunit of the channel inducing the hypertrophy.

It is understood that the primary structure of the pore-forming L-type $Ca^{2+}$ channel alpha-1 ($\alpha_1$) subunit is composed of 4 homologous repeating motifs (I-IV), each of which consists of 6 putative transmembrane segments (S1-S6) (FIG. 1). Cytoplasmic loops between the transmembrane segments are named according to the motifs they link. There are also $\alpha_2$, δ and γ subunits which are extracellular subunits linked to the alpha subunit via a disulphide bridge, and the L-type $Ca^{2+}$ channel beta-2 ($\beta_2$) subunit which is entirely intracellular. The structure of the $\beta_2$ subunit may be expressed as any of four beta subunit isoforms ($\beta_1$-$\beta_4$). All isoforms are hydrophilic, nonglycosylated, and intracellular with no membrane-spanning region. The $\beta_2$ isoform is tightly bound to a highly conserved motif in the cytoplasmic linker between repeats I and II of all cloned high voltage-activated $\alpha_1$ subunit isoforms, called the alpha-interaction domain (AID).

The L-type $Ca^{2+}$ channels also play an important role in regulating mitochondrial function, and this involves both calcium-dependent and calcium-independent mechanisms. Activation of the L-type $Ca^{2+}$ channel with voltage-clamp of the plasma membrane or with DHP receptor agonist BayK (−) is sufficient to increase intracellular and mitochondrial calcium, NADH production, superoxide production and metabolic activity in wt cardiac myocytes, in a calcium-dependent manner. Activation of the L-type $Ca^{2+}$ channel also causes an increase in mitochondrial membrane potential (ψm), in a calcium-independent manner. This response is attenuated in the presence of F-actin depolymerizing agents, indicating that the response is in part dependent on an interaction between the L-type $Ca^{2+}$ channel and mitochondria, via F-actin. The L-type $Ca^{2+}$ channel influences mitochondrial function through a structural-functional communication between the L-type $Ca^{2+}$ channel and mitochondria via the cytoskeletal network, following conformational changes in L-type $Ca^{2+}$ channel that occur on a beat-to-beat basis.

Patients with HCM exhibit altered communication between the L-type $Ca^{2+}$ channel and mitochondria and altered metabolic activity. Specifically, cTnI-G203S myocytes exhibit a faster L-type $Ca^{2+}$ channel inactivation rate, and increased ψm and mitochondrial metabolic activity (consistent with the human condition) in response to activation of the L-type $Ca^{2+}$ channel. These alterations also occur in myocytes isolated from hearts of cTnI-G203S mice that have not yet developed the cardiomyopathy, indicating that alterations in the L-type $Ca^{2+}$ channel kinetics and metabolic activity precede development of the cardiomyopathy.

The alpha subunit of the channel has been the target of a number of therapies which aim to protect the cardiac muscle during reperfusion and calcium overload. Examples of these therapies include monoclonal antibodies to the alpha subunit; Ca2+ channel antagonists such as the Dihydropyridines, the Benzothiazepines and the Phenylalkylamines. Although Ca2+ channel blockers bind specifically to regions of the α1C subunit of the L-type Ca2+ channel, these drugs have been found to have limited success because they can induce myocardial depression and heart failure.

AID-Peptide

In WO/2013/113060, the inventors made the observation that restricting the movement of the $\beta_2$ subunit of the L-type $Ca^{2+}$ channel with a peptide derived against AID prevented interaction of $\beta_2$ and $\alpha_1$ subunits. The inventors hypothesised in WO/2013/113060 that the β-interaction domain (BID) interacts with the AID through a conserved hydrophobic cleft, termed the alpha-binding pocket (ABP). The I-II loop of the $\alpha_1$ subunit contains an endoplasmic reticulum retention signal that restricts cell surface expression. The $\beta_2$ subunit reverses the inhibition imposed by the retention signal and is able to modulate the biophysical properties of the L-type $Ca^{2+}$ channels $\alpha_1$ subunit, producing a leftward shift of the current-voltage relationship, which is consistent with the involvement of the S4 region of the $\alpha_1$ subunit voltage-sensor region.

As set out in WO/2013/113060, the inventors developed a peptide of sequence QQLEEDLKGYLDWITQAE (SEQ ID NO: 1), (AID peptide) that interacts with the BID of a L-type $Ca^{2+}$ channel $\beta_2$ subunit in a heart muscle cell, thereby preventing interaction of that $\beta_2$ subunit with the AID of an L-type $Ca^{2+}$ channel $\alpha_1$ subunit. The peptide-bound $\beta_2$ subunit is unable to reverse the inhibition on the di subunit imposed by the endoplasmic reticulum retention signal which restricts cell surface expression of the di subunit. This results in a restriction on the activation of the L-type $Ca^{2+}$ channel and decreases mitochondrial energy consumption.

However, there remains a need for the development of additional peptides with improved potency in disrupting the interaction of the $\beta_2$ subunit with the AID of an L-type $Ca^{2+}$ channel in order to effectively treat or prevent cardiac hypertrophy.

SUMMARY OF INVENTION

Inventors have found that the activity of the AID peptide is dependent on the composition of the peptide. In particular, the inventors have identified that limited substitution of the third and seventh amino acid in the AID peptide sequence has an unexpected impact on the disruptive capacity that this peptide creates in the interaction of the $\beta_2$ subunit with the AID of an L-type $Ca^{2+}$.

Accordingly, in a first aspect, the invention provides a peptide comprising the amino acid sequence:

(SEQ ID NO: 2)
QQ$X_1$EED$X_2$KGYLDWITQAE wherein $X_1$ is an amino acid selected from the group comprising: Q, E or R; and wherein $X_2$ is an amino acid selected from the group comprising: L or E or a variant thereof. Preferably, the peptide does not consist of SEQ ID NO: 1.

Preferably, the invention provides a peptide comprising the amino acid sequence:

QQ$X_1$EED$X_2$KGYLDWITQAE wherein $X_1$ is an amino acid selected from the group comprising: Q, E or R; and wherein $X_2$ is an amino acid selected from the group comprising: L or E;

or a variant thereof, wherein the peptide does not consist of SEQ ID NO: 1.

Preferably, the peptide binds to the BID of a L-type $Ca^{2+}$ channel $\beta_2$ subunit. More preferably, the peptide binds to the BID of a human L-type $Ca^{2+}$ channel $\beta_2$ subunit.

Preferably, the invention provides a peptide comprising any one of the amino acid sequences of SEQ ID NO: 4-7 or a variant thereof, wherein the peptide does not consist of SEQ ID NO: 1. Preferably, the peptide binds to the BID of a L-type $Ca^{2+}$ channel $\beta_2$ subunit. More preferably, the peptide binds to the BID of a human L-type $Ca^{2+}$ channel $\beta_2$ subunit.

In a second aspect, the invention provides a peptide comprising: a peptide portion comprising the amino acid sequence of SEQ ID NO: 2; and a peptide portion comprising the amino acid sequence of:

(SEQ ID NO: 3)
RKKRRQRRRZaa wherein Zaa is a 6-amino hexanoic acid or a variant thereof. Preferably, the peptide binds to the BID of a L-type $Ca^{2+}$ channel $\beta_2$ subunit. More preferably, the peptide binds to the BID of a human L-type $Ca^{2+}$ channel $\beta_2$ subunit.

Preferably, the peptide of the invention comprises an amino acid sequence selected from the group of at least 75%; at least 80%; at least 85%; at least 90%; at least 95%; at least 96%; at least 97%; at least 98%; and at least 99% sequence homology to a peptide comprising SEQ ID NO: 2. More preferably, the peptide of the invention comprises an amino acid sequence comprising one or more conservative amino acid substitutions to SEQ ID NO: 2 selected from the suitable amino acid substitutions set out in Table 3.

In a third aspect, the invention provides a method for modulating movement of a beta subunit of the L-type $Ca^{2+}$ channel in a cardiac cell of a subject, comprising administering to the subject a peptide of the invention.

In a fourth aspect, the invention provides a method for modulating binding of a beta subunit of the L-type $Ca^{2+}$ channel in a cardiac cell of a subject, comprising administering to the subject a peptide of the invention.

Preferably, the peptide prevents interaction between the beta subunit of the L-type $Ca^{2+}$ channel and an alpha subunit of the L-type $Ca^{2+}$ channel in a cardiac cell of a subject and therefore activation of the channel.

In a fifth aspect, the invention provides a method for modulating a L-type $Ca^{2+}$ channel in a cardiac cell of a subject, comprising the step of administering to the subject a peptide of the invention.

In a sixth aspect, the invention provides a method for treating, preventing or reducing myocardial damage and/or oxidative stress in the heart of a subject, comprising the step of administering to the subject a peptide of the invention.

Preferably the myocardial damage comprises cardiac hypertrophy. Preferably, cardiac hypertrophy and/or oxidative stress is reduced. More preferably, intracellular $Ca^{2+}$ levels in a cardiac cell in the heart of the subject are slightly reduced or substantially maintained in a cardiac cell in the heart of the subject. The subject is preferably a mammal and is more preferably a human. Most preferably, the subject suffers from hypertrophic cardiomyopathy.

In a seventh aspect, the invention provides a method for treating or preventing cardiac hypertrophy in a subject comprising the step of administering to the subject a peptide of the invention. Preferably, the subject suffers from hypertrophic cardiomyopathy.

In an eighth aspect, the invention provides a use of a peptide of the invention for modulating movement of a beta subunit of the L-type $Ca^{2+}$ channel in a cardiac cell in the heart of a subject.

In a ninth aspect, the invention provides a use of a peptide of the invention for modulating a L-type $Ca^{2+}$ channel in a cardiac cell of a subject.

In a tenth aspect, the invention provides a use of a peptide of the invention for treating, preventing or reducing myocardial damage and/or oxidative stress in the heart of a subject. Preferably, the use is during and/or following reperfusion.

In an eleventh aspect, the invention provides a polynucleotide encoding a peptide of the invention described herein.

In a twelfth aspect, the invention provides the use of the peptide of the invention for the manufacture of a medicament to treat, prevent, or ameliorate myocardial damage and/or oxidative stress in the heart of a subject. Preferably, the myocardial damage is cardiac hypertrophy.

In a thirteenth aspect, the invention provides a pharmaceutical, prophylactic or therapeutic composition comprising the peptide of the invention; and one or more pharmaceutically acceptable carriers and/or diluents.

In a fourteenth aspect, the invention provides a method for slowing the progression of myocardial fibrosis in a subject comprising the step of administering to the subject a peptide of the invention.

In a fifteenth aspect, the invention provides the use of a peptide of the invention for slowing the progression of myocardial fibrosis in a subject In a sixteenth aspect, the invention provides a kit to treat, prevent or ameliorate the effects of myocardial damage and/or oxidative stress in the heart of a subject, wherein the kit comprises at least a peptide of the invention, packaged in a suitable container, together with instructions for its use.

In a seventeenth aspect, the invention provides a use of a peptide of the invention for modulating binding to a L-type $Ca^{2+}$ channel alpha-interacting domain in a cardiac cell of a subject.

In an eighteenth aspect, the invention provides the use of the peptide of the invention for the manufacture of a medicament to treat, prevent, or ameliorate reperfusion injury in the heart of a subject.

Further features of the present invention are more fully described in the following description of several non-limiting embodiments thereof. This description is included solely for the purposes of exemplifying the present invention. It should not be understood as a restriction on the broad summary, disclosure or description of the invention as set out above.

BRIEF DESCRIPTION OF THE FIGURES

The description will be made with reference to the accompanying drawings.

FIG. 3 illustrates the effect of mutant peptides on oxidative stress responses in wild type cardiac myocytes.

FIG. 7 presents a table of sequences referenced in this application.

FIG. 8 presents the echocardiographic parameters of cTnI-G203S mice administered with 10 μM AID(S)-TAT or AID-TAT.

FIG. 16 illustrates that the in vivo treatment of cTnI-G203S mice with AID-TAT variant peptides slows the progression of hypertrophy.

SEQUENCE LISTING

Figure 1:
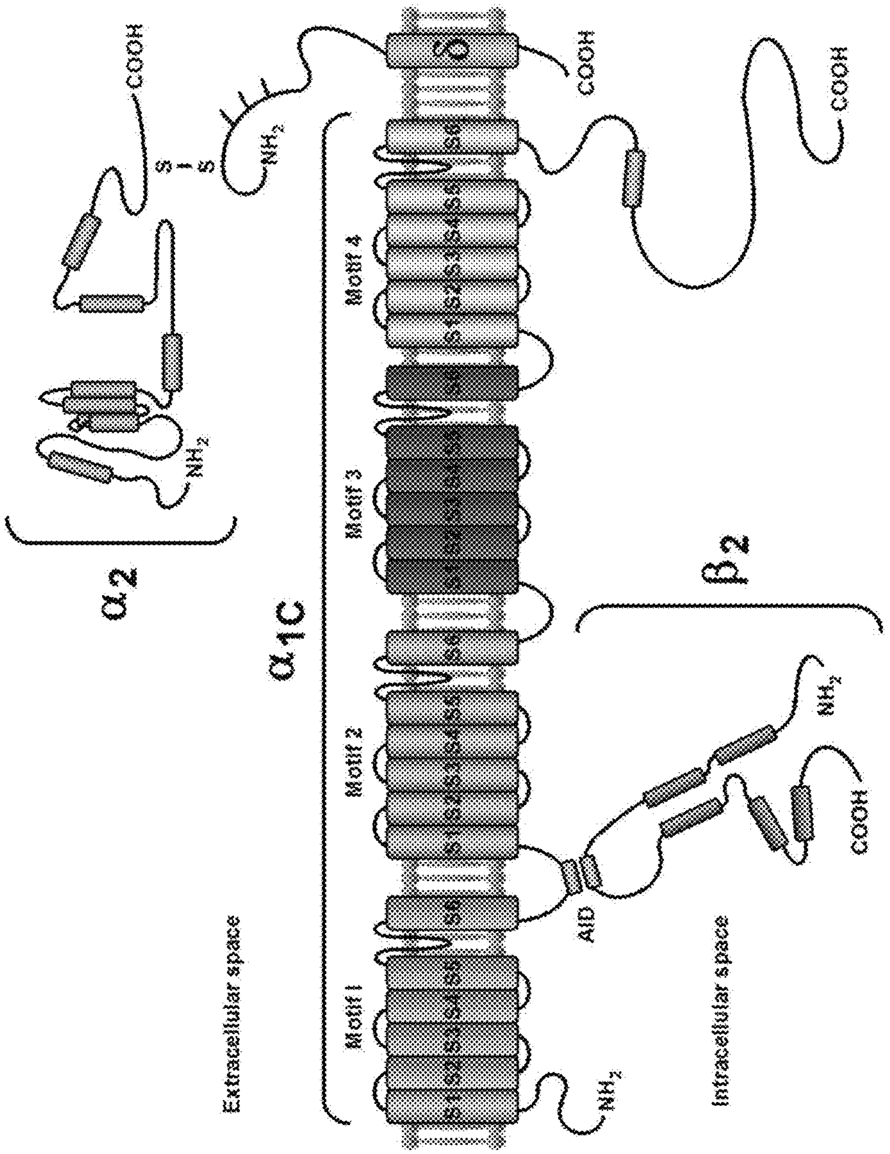
FIG. 1 presents an illustration of the primary structure of the pore-forming L-type $Ca^{2+}$ channel alpha-1 ($\alpha_1$) subunit which is composed of 4 homologous repeating motifs (I-IV), each of which consists of 6 putative transmembrane segments (S1-S6). $\alpha_2\delta$ consists of a transmembrane protein ($\delta$) and extracellular $\alpha_2$ protein linked via a disulfide bond (S—S). $\beta_2$ is an intracellular protein bound to the linker between motifs 1 and 2 of $\alpha_{1C}$ via the $\alpha$-interacting domain (AID).

Table 1 below sets out a list of sequences referred to in this specification:

| SEQ ID NO | Name | Sequence |
|---|---|---|
| SEQ ID NO: 1 | AID Peptide | QQLEEDLKGYLDWITQAE |
| SEQ ID NO: 2 | Variant AID Peptide | $QQX_1EEDX_2KGYLDWITQAE$ |
| SEQ ID NO: 3 | TAT Peptide | RKKRRQRRRZaa |
| SEQ ID NO: 4 | Variant P7 | QQQEEDLKGYLDWITQAE |
| SEQ ID NO: 5 | Variant P14 | QQEEEDLKGYLDWITQAE |
| SEQ ID NO: 6 | Variant P15 | QQEEEDEKGYLDWITQAE |
| SEQ ID NO: 7 | Variant P16 | QQREEDLKGYLDWITQAE |
| SEQ ID NO: 8 | Nuclear Localisation Signal | GRKKR |
| SEQ ID NO: 9 | Protein transduction domain | YGRKKRRQRRR |
| SEQ ID NO: 10 | AID[S] Peptide | QKILGEWDLAQYTDQELE |
| SEQ ID NO: 11 | Variant P1 | DLKGYLDWITQAE |
| SEQ ID NO: 12 | Variant P4 | LEEDLKGYLDWITQAE |
| SEQ ID NO: 13 | Variant P6 | KGYLDWITQAE |
| SEQ ID NO: 14 | Variant P10 | DLKGYLDWITQA |
| SEQ ID NO: 15 | Variant P11 | DLKGYLDWITQ |
| SEQ ID NO: 16 | Variant P12 | DLKGYLDWIT |
| SEQ ID NO: 17 | Variant P13 | QQLEEDLKGFLDAATQAE |

DESCRIPTION OF EMBODIMENTS

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range which lead to the same or substantially the same outcome as the values immediately adjacent to that value which defines the boundary to the range.

Features of the invention will now be discussed with reference to the following non-limiting description and examples.

Variant AID Peptide

The present invention provides a peptide comprising the amino acid sequence:

(SEQ ID NO: 2)
$QQX_1EEDX_2KGYLDWITQAE$ wherein $X_1$ is an amino acid selected from the group comprising: Q, E or R; and wherein $X_2$ is an amino acid selected from the group comprising: L or E Preferably the peptide binds to the BID of a L-type $Ca^{2+}$ channel β2 subunit. More preferably, the peptide binds to the BID of a human L-type $Ca^{2+}$ channel $\beta_2$ subunit. Most preferably, the peptide binds to the BID of a L-type $Ca^{2+}$ channel $\beta_2$ subunit with greater affinity compared with SEQ ID NO: 1.

The present invention provides an isolated peptide comprising variants to the highly conserved AID motif of the human L-type $Ca^{2+}$ channel $\alpha_1$ subunit (SEQ ID NO:1).

Surprisingly, the inventors have identified a number of variants to specific amino acids in the original AID-peptide that improve the binding affinity of the peptide to BID of a L-type $Ca^{2+}$ channel $\beta_2$ subunit.

In an aspect, the improvements in binding affinity result in improved functionality of the peptide in vitro and/or in vivo. In an aspect, the peptides of the invention can further slow the inactivation rate of the L-type $Ca^{2+}$ channel in comparison to the original-AID peptide. In another aspect, the peptides of the invention can be administered at a lower dose to the subject in comparison to the original-AID peptide to produce the same effect in vitro or in vivo.

The inventors have identified specific variations at positions $X_1$ and $X_2$ are effective at increasing the binding affinity of the peptide to BID in comparison with the original-AID peptide. For example, the original AID-peptide has hydrophobic amino acid leucine at position $X_1$, but in some embodiments, variations at position $X_1$ to a negative (e.g. glutamic acid), positive (e.g. arginine) or polar uncharged (e.g. glutamine) amino acids, each increase binding affinity of the peptide to BID in comparison with the original-AID peptide.

Binding affinity of the peptides of the invention to the BID can be measured by a number of techniques that are well known in the art, including SDS-PAGE assays.

Preferably, the peptide is provided in a pharmaceutically acceptable form.

Preferably the peptide is not QQLEEDLKGYLDWITQAE (SEQ ID NO: 1).

Preferably the peptide is not toxic. Most preferably, the peptide does not exhibit kidney toxicity and/or liver toxicity. Kidney toxicity can be measured by methods known in the art, including by assessing urea and creatinine concentrations using the Quantichrom Urea assay kit (BioAssay Systems, Hayward, CA) and Quantichrom Creatinine assay kit (BioAssay Systems, Hayward, CA), respectively. Liver toxicity can be measured by methods known in the art including by assessing alanine transaminase (ALT) and aspartate transaminase (AST) concentrations using the Alanine Transaminase assay kit (BioAssay Systems, Hayward, CA) and Aspartate Transaminase assay kit (BioAssay Systems, Hayward, CA), respectively.

The present invention further and more preferably provides a peptide comprising the amino acid sequence of SEQ ID NO: 4-7 as set out in the table below:

TABLE 2

| SEQ ID NO | Peptide | Amino Acid Sequence |
|---|---|---|
| SEQ ID NO: 4 | Variant P7 | QQQEEDLKGYLDWITQAE |
| SEQ ID NO: 5 | Variant P14 | QQEEEDLKGYLDWITQAE |
| SEQ ID NO: 6 | Variant P15 | QQEEEDEKGYLDWITQAE |
| SEQ ID NO: 7 | Variant P16 | QQREEDLKGYLDWITQAE |

A peptide of the present invention may be recombinant, natural or synthetic. A peptide of the invention may be mixed with diluents, adjuvants or carriers (including nanoparticles) that will not interfere with the intended purpose of the peptide. A peptide of the invention may also be in a substantially purified form, in which case it will generally comprise the peptide in a preparation in which at least 90%, 95%, 98% or 99% of the protein in the preparation is a peptide of the invention. The term 'peptide' as used herein may be used interchangeably with the term 'polypeptide' as referring to a chain of at least two amino acid monomers.

In some embodiments, the peptides of the invention comprise one or more repeats of a peptide portion comprising SEQ ID NO:2 or a variant thereof.

Variants

The present invention further includes variants of; (1) the amino acid sequence of SEQ ID NO: 2; or (2) the amino acid sequence of SEQ ID NO: 2 and SEQ ID NO: 3. Preferably, the variant binds to the BID of a L-type $Ca^{2+}$ channel $\beta_2$ subunit. More preferably, the peptide binds to the BID of a human L-type $Ca^{2+}$ channel $\beta_2$ subunit. Most preferably, the variant binds with a higher affinity to the BID of a L-type $Ca^{2+}$ channel $\beta_2$ subunit compared with SEQ ID NO: 1.

Preferably the variant has an amino acid sequence homology to (1) the amino acid sequence of SEQ ID NO: 2; or (2) the amino acid sequence of SEQ ID NO: 2 and SEQ ID NO: 3 selected from the group consisting of: at least 75% sequence homology; at least 80%; at least 85%; at least 90%; at least 95%; at least 96%; at least 97%; at least 98%; and at least 99%. Preferably, the variant is not QQLEEDLKGYLDWITQAE.

The term "% sequence homology", as used here, may for example be calculated as follows. The query sequence is aligned to the target sequence using the CLUSTAL W algorithm (Thompson et al, Nucleic Acids Research, 22:4673-4680 (1994)). A comparison is made over the window corresponding to one of the aligned sequences, for example the shortest. The window may in some instances be defined by the target sequence. In other instances, the window may be defined by the query sequence. The amino acid residues at each position are compared, and the percentage of positions in the query sequence that have identical correspondences in the target sequence is reported as % sequence homology.

Variants of (1) the amino acid sequence of SEQ ID NO: 2; and (2) the amino acid sequence of SEQ ID NO: 2 and SEQ ID NO: 3 include a polypeptide substantially homologous to (1) the amino acid sequence of SEQ ID NO: 2; or (2) the amino acid sequence of SEQ ID NO: 2 and SEQ ID NO: 3 but which has an amino acid sequence different from that of (1) the amino acid sequence of SEQ ID NO: 2; or (2) the amino acid sequence of SEQ ID NO: 2 and SEQ ID NO: 3 sequence because one or more amino acids have been chemically modified or substituted by amino acids analogs. Preferably, any changes to the sequence to create a variant of (1) the amino acid sequence of SEQ ID NO: 2; or (2) the amino acid sequence of SEQ ID NO: 2 and SEQ ID NO: 3 can also include, in addition to amino acid substitutions, amino acid deletions and/or amino acid additions.

Amino acid substitutions are preferably conservative amino acid substitutions known to those skilled in the art. For example, the person skilled in the art may perform an amino acid substitution by selecting an amino acid from within the same class of amino acid that is shared with the specific amino acid that is identified for substitution. Examples of suitable amino acid substitutions are presented in Table 3 below.

TABLE 3

| Amino acids | Examples of conservative substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine |

TABLE 3-continued

| Amino acids | Examples of conservative substitutions |
|---|---|
| Leu (L) | Ile, Val, Met, Ala, Phe, Norleucine |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile Met, Leu, Phe, Ala, Norleucine |

Peptide variants of the present invention also include fusion to further peptides, for example, where an additional peptide sequence is fused to a peptide of the invention to aid in extraction and purification. Examples of additional fusion peptide partners include glutathione-S-transferase (GST), hexahistidine, GAL4 (DNA binding and/or transcriptional activation domains) and β-galactosidase. It may also be convenient to include a proteolytic cleavage site between the additional peptide partner and the peptide of the invention to allow removal of additional peptide sequences. Preferably the additional peptide will not hinder binding of the peptide of the invention to the BID of a L-type $Ca^{2+}$ channel $\beta_2$ subunit.

AID-TAT Fusion Peptide

In a preferred form, the invention further provides a peptide comprising:

a peptide portion comprising the amino acid sequence of SEQ ID NO: 2; and a peptide portion comprising the amino acid sequence:

(SEQ ID NO: 3)
RKKRRQRRRZaa wherein Zaa is 6-amino hexanoic acid or a variant thereof.

The peptide portion of the peptide of the invention comprising the amino acid sequence of SEQ ID NO: 3 encodes a TAT peptide. Trans-activating transcriptional activator (TAT) from Human Immunodeficiency Virus 1 is a cell-penetrating peptide which is known in the art to deliver attached molecules such as peptides into cells. Thus, not wishing to be bound by any particular mechanism, it is believed the TAT peptide portion in the peptide of the invention facilitates transport of the peptide into cardiac cells via endocytosis or by direct translocation across the plasma membrane. The nuclear localisation signal found within the domain, GRKKR (SEQ ID NO: 8), mediates further translocation of TAT into the cell nucleus. The biological role of this domain and exact mechanism of transfer is currently unknown. The amino acid sequence of the protein transduction domain is YGRKKRRQRRR (SEQ ID NO: 9).

However, the peptide of the invention may comprise other or additional peptide portions which assist or facilitate in the transport of the peptide into cardiac or other cells, or provide some other benefit, for example, amongst others, identifying the location of a peptide of the invention within a cell.

In some embodiments, the peptides of the invention comprise one or more repeats of a peptide portion comprising SEQ ID NO:2 and a peptide portion comprising SEQ ID NO: 3 or a variant thereof.

Polynucleotides

The present invention also provides an isolated polynucleotide encoding a peptide of the present invention as described herein including peptides comprising SEQ ID No: 2-7. It will be understood by a skilled person that due to the degeneracy of the amino acid code, numerous different polynucleotides can encode the same peptide as a result of the degeneracy of the genetic code. In addition, it is to be understood that skilled persons may, using routine techniques, make nucleotide substitutions that do not affect the peptide sequence encoded by the polynucleotides of the invention to reflect the codon usage of any particular host organism in which the polypeptides of the invention are to be expressed.

Polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand. They may also be polynucleotides that include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Reference to "isolated" polynucleotide(s) means a polynucleotide, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution.

Isolated RNA molecules include in vivo or in vitro RNA transcripts of the DNA molecules of the present invention. Isolated peptides of the present invention further include such molecules produced synthetically.

As indicated above, the polynucleotides of the present invention that encode a peptide of the present invention include, but are not limited to, those peptides encoded by the amino acid sequences of SEQ ID No: 2 and 4-7. Rather the polynucleotides of the present invention may comprise the coding sequence for the peptides and additional sequences, such as those encoding a leader or secretory sequence, such as a pre-, or pro- or prepro-protein sequence; the coding sequence of the peptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example ribosome binding and stability of mRNA; an additional coding sequence which codes for additional amino acids, such as those which provide additional functionalities. Preferably, the additional sequence comprises the peptide encoded by the amino acid sequences of SEQ ID No: 3. Polynucleotides according to the present invention also include those encoding a peptide lacking the N terminal methionine.

The present invention further relates to variants of the nucleic acid molecules of the present invention, which encode variants of the peptides of the present invention.

Such variants include those produced by nucleotide substitutions, deletions or additions that may involve one or more nucleotides. Non-naturally occurring variants may be produced using mutagenesis techniques known to those in the art. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the encoded peptide. Also especially preferred in this regard are conservative substitutions.

It will be further recognized in the art that, for such nucleic acid molecules that are not degenerate variants, a reasonable number will also encode a peptide of the invention having one or more properties of the full polypeptide such as being able to interact with the BID of a L-type $Ca^{2+}$ channel $\beta_2$ subunit. This is because the skilled artisan is fully aware of amino acid substitutions that are either less likely or not likely to significantly effect protein function (e.g., replacing one aliphatic amino acid with a second aliphatic amino acid).

Vectors and Host Cells

A nucleic acid molecule encoding the amino acid sequence of a peptide of the invention may be inserted into an appropriate expression vector using standard ligation techniques. The vector is typically selected to be functional in the particular host cell employed (i.e., the vector is compatible with the host cell machinery such that amplification of the nucleic acid molecule and/or expression of the nucleic acid molecule can occur). A nucleic acid molecule encoding the amino acid sequence of a peptide of the invention may be amplified/expressed in prokaryotic, yeast, insect (baculovirus systems), and/or eukaryotic host cells. Selection of the host cell will depend in part on whether the peptide is to be post-translationally modified (e.g., glycosylated and/or phosphorylated). If so, yeast, insect, or mammalian host cells are preferable.

Typically, expression vectors used in any of the host cells will contain sequences for plasmid maintenance and for cloning and expression of exogenous nucleotide sequences. Such sequences, collectively referred to as "flanking sequences" in certain embodiments, will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for secretion of the peptide, a ribosome binding site, a polyadenylation sequence, a polylinker region for inserting the nucleic acid encoding the peptide to be expressed, and a selectable marker element.

Preferred vectors for practicing this invention are those that are compatible with bacterial, insect, and mammalian host cells. Such vectors include, inter alia, pCRII, pCR3, and pcDNA3.1 (Invitrogen Company, Carlsbad, CA), pBSII (Stratagene Company, La Jolla, CA), pET15 (Novagen, Madison, WI), pGEX (Pharmacia Biotech, Piscataway, NJ), pEGFP-N2 (Clontech, Palo Alto, CA), pETL (BlueBacII; Invitrogen), pDSR-alpha (PCT Publication No. WO 90/14363) and pFastBacDual (Gibco/BRL, Grand Island, NY).

Additional suitable vectors include, but are not limited to, cosmids, plasmids or modified viruses, but it will be appreciated that the vector system must be compatible with the selected host cell. Such vectors include, but are not limited to, plasmids such as Bluescript® plasmid derivatives (a high copy number ColE1-based phagemid, Stratagene Cloning Systems Inc., La Jolla CA), PCR cloning plasmids designed for cloning Taq-Taq-amplified PCR products (e.g., TOPO™ TA Cloning® Kit, PCR2.1® plasmid derivatives, Invitrogen, Carlsbad, CA), and mammalian, yeast, or virus vectors such as a baculovirus expression system (pBacPAK plasmid derivatives, Clontech, Palo Alto, CA).

After the vector has been constructed and a polynucleotide molecule encoding a peptide of the invention has been inserted into the proper site of the vector, the completed vector may be inserted into a suitable host cell for amplification and/or fusion protein expression. The transformation of an expression vector for a peptide of the invention into a selected host cell may be accomplished by well-known methods including transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast cell, an insect cell or a vertebrate cell). The host cell, when cultured under appropriate conditions, synthesizes the peptide that can subsequently be collected from the culture medium (if the host cell secretes it into the medium) or directly from the host cell producing it (if it is not secreted). The selection of an appropriate host cell will depend upon various factors, such as desired expression levels, peptide modifications that are desirable or necessary for activity, such activity (such as glycosylation or phosphorylation), and ease of folding into a biologically active molecule.

A number of suitable host cells are known in the art and many are available from the American Type Culture Collection (ATCC), 10801 University Boulevard, Manassas, VA 20110-2209. Examples include, but are not limited to, mammalian cells, such as Chinese hamster ovary cells (CHO) (ATCC No. CCL61); CHO DHFR-cells (Urlaub et al., *Proc. Natl. Acad. Sci. USA,* 97:4216-4220 (1980)); human embryonic kidney (HEK) 293 or 293T cells (ATCC No. CRL1573); or 3T3 cells (ATCC No. CCL92). The selection of suitable mammalian host cells and methods for transformation, culture, amplification, screening and screening, product production and purification are known in the art. Other suitable mammalian cell lines are the monkey COS-1 (ATCC No. CRL1650) and COS-7 cell lines (ATCC No. CRL1651) cell lines, and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene or may contain a dominantly acting selection gene. Other suitable mammalian cell lines include, but are not limited to, mouse neuroblastoma N2A cells, HeLa, mouse L-L-929 cells, 3T3 lines derived from Swiss, Balb-c or NIH mice, BHK or Hak hamster cell lines, which are available from the ATCC. Each of these cell lines is known by and available to those skilled in the art of protein expression.

Similarly, useful as host cells suitable for the present invention are bacterial cells. For example, the various strains of *E. coli* (e.g., HB101, (ATCC No. 33694) DH5α, DH10, and MC1061 (ATCC No. 53338)) are well-well known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of peptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques,* 14:810-817 (1993); Lucklow, *Curr. Opin. Biotechnol.,* 4:564-572 (1993); and Lucklow et al. (*J. al., J. Virol.,* 67:4566-4579 (1993). Preferred insect cells are Sf-9 and Hi5 (Invitrogen, Carlsbad, CA).

One may also use transgenic animals to express glycosylated peptides of the invention. For example, one may use a transgenic milk-producing animal (a cow or goat, for example) and obtain the present glycosylated peptide in the animal milk. One may also use plants to produce peptides of the invention. However, in general, the glycosylation occurring in plants is different from that produced in mammalian cells, and may result in a glycosylated product which is not suitable for human therapeutic use.

Therapeutic Compositions

Therapeutic compositions are within the scope of the present invention. Peptides of the invention can be combined with various components to produce compositions of the invention. Such compositions can comprise a therapeutically effective amount of a peptide or nucleotide of the invention in admixture with a pharmaceutically or physiologically acceptable formulation agent selected for suitability with the mode of administration. Pharmaceutical compositions may also comprise a therapeutically effective amount of one or more peptide of the invention in admixture with a pharmaceutically or physiologically acceptable formulation agent selected for suitability with the mode of administration. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. See, e.g., Remington's Pharmaceutical Sciences, 19th Ed. (1995, Mack Publishing Co., Easton, Pa.) which is herein incorporated by reference.

The pharmaceutical composition can contain formulation materials for modifying, maintaining or preserving, for example, the pH, osmolarity, viscosity, clarity, colour, isotonicity, odour, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulphite or sodium hydrogen-sulphite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin), fillers; monosaccharides, disaccharides; and other carbohydrates (such as glucose, mannose, or dextrins); proteins (such as serum albumin, gelatin or immunoglobulins); colouring, flavouring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapol); stability enhancing agents (sucrose or sorbitol); tonicity enhancing agents (such as alkali metal halides, preferably sodium or potassium chloride), delivery vehicles, diluents, excipients and/or pharmaceutical adjuvants.

The optimal pharmaceutical composition will be determined by one skilled in the art depending upon, for example, the intended route of administration, delivery format, and desired dosage. Such compositions may influence the physical state, stability, rate of in vivo release, and rate of in vivo clearance of the peptide of the invention. The preferred form of the pharmaceutical composition depends on the intended mode of administration and therapeutic application. Pharmaceutical compositions prepared according to the invention may be administered by any means that leads to the peptides of the invention coming in contact with a causative agent of a disease or disorder as herein described including cardiac hypertrophy or oxidative stress.

The primary vehicle or carrier in a pharmaceutical composition may be either aqueous or non-aqueous in nature. For example, a suitable vehicle or carrier may be water for injection, physiological saline solution, solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefor. In one embodiment of the present invention, pharmaceutical compositions may be prepared for storage by mixing the selected composition having the desired degree of purity with optional formulation agents in the form of a lyophilized cake or an aqueous solution. Further, the peptide product may be formulated as a lyophilizate using appropriate excipients such as sucrose.

The pharmaceutical compositions can be capable of parenteral delivery. Alternatively, the compositions may be capable of delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired peptide of the invention in a pharmaceutically acceptable vehicle. A particularly suitable vehicle for parenteral injection is sterile distilled water in which the active agent is formulated as a sterile, isotonic solution, properly preserved. Yet another preparation can involve the formulation of the desired molecule with an agent, such as injectable microspheres, bio-erodible particles, polymeric compounds (such as polylactic acid, acid or polyglycolic acid), or beads or liposomes, that provides for the controlled or sustained release of the product which may then be delivered as a depot injection. Hyaluronic acid may also be used, and this may have the effect of promoting sustained duration in the circulation. Other suitable means for the introduction of the desired molecule include implantable drug delivery devices.

It is also contemplated that certain formulations may be administered orally. In one embodiment of the present invention, peptides of the present invention that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized, and pre-systemic degradation is minimized. Additional agents can be included to facilitate absorption of the active agent. Diluents, flavourings, low melting point waxes, vegetable oils, lubricants, suspending agents, tablet disintegrating agents, and binders may also be employed.

Another pharmaceutical composition may involve an effective quantity of a peptide of the invention in a mixture with non-toxic excipients that are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a peptide of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT Application No. PCT/US93/00829 that describes the controlled release of porous polymeric microparticles for the delivery of pharmaceutical compositions. Additional examples of sustained-sustained-release preparations include semipermeable polymer matrices in the form of shaped articles, for example, films, or microcapsules. Sustained release matrices may include polyesters, hydrogels, polylactides, copolymers of L-glutamic acid and gamma ethyl-L-glutamate, ethylene vinyl acetate or poly-D(−)-3-hydroxybutyric acid. Sustained-release compositions may also include liposomes, which can be prepared by any of several methods known in the art.

The pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

The effective amount of the active agent in the pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the active agent is being used, the route of administration, and the size (body weight, body surface or organ size) and condition (the age and general health) of the patient. Accordingly, the clinician may titre the dosage and modify the route of administration to obtain the optimal therapeutic effect. A typical dosage may range from about 0.1 μg/kg to up to about 100 mg/kg or more, depending on the factors mentioned above. In other embodiments, the dosage may range from 0.1 μg/kg up to about 100 mg/kg; or 1 μg/kg up to about 100 mg/kg; or 5 μg/kg up to about 100 mg/kg.

The frequency of dosing will depend upon the pharmacokinetic parameters of the active agent and the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The peptide or pharmaceutical composition comprising the peptide can be administered to the subject in a range of treatment regimens. For example, the peptide or pharmaceutical composition can be administered hourly, three times daily, twice daily, once daily, once every two days, once every three days, once weekly, once every two weeks, once monthly, once every two months, once every six months, and once yearly. The appropriate regimen can be determined by the person skilled in the art based on the nature of the condition to be treated. For example, the peptide or pharmaceutical composition comprising the peptide can be administered three times per week.

The route of administration of the pharmaceutical composition is in accord with known methods, e.g., orally, through injection by intravenous, intracoronary, intraperitoneal, intracerebral (intra-parenchymal), intracerebroventricular, intramuscular, intra-ocular, intraarterial, intraportal, or intralesional routes; by sustained release systems or by implants. Where desired, the compositions may be administered by bolus injection or continuously by infusion, or by implantation device.

Alternatively or additionally, the composition may be administered locally via implantation of a membrane, sponge or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use the pharmaceutical compositions herein in an ex vivo manner. In such instances, cells, tissues, or organs that have been removed from the patient are exposed to the pharmaceutical compositions after which the cells, tissues and/or organs are subsequently implanted back into the patient.

In another form, nanoparticles may be employed as carriers for delivery of peptides of the invention. For example, the nanoparticles may be spherical polymeric nanoparticles. Nanoparticles have been shown to overcome some limitations of conventional therapeutic delivery such as nonspecific biodistribution and targeting, and lack of water solubility, amongst others. Thus, nanoparticles may be used for delivering peptides of the invention to cardiac cells for treatment of a patient with the peptides.

In an aspect, the peptides of the invention are delivered through the use of dendronized polymers. Preferably, the peptides of the invention are delivered through the use of linear dendronized polymers (denpols). Most preferably, the peptides of the invention are complexed with linear deondronized polymers to form polymer-peptide nanoparticles. The polymer-peptide nanoparticles can be delivered intracellularly.

The routes of administration described herein are intended only as a guide since a skilled practitioner will be able to determine readily the optimum route of administration and dosage for any particular patient.

Uses and Methods for Peptides of the Invention

The invention provides a use of a peptide comprising: the amino acid sequence of SEQ ID NO: 2, or variants thereof; or the amino acid sequence of SEQ ID NO: 2 and SEQ ID NO: 3, or variants thereof; for modulating binding to a L-type $Ca^{2+}$ channel alpha-interacting domain. This preferably occurs intracellularly in a cardiac cell.

The invention provides a use of a peptide comprising: the amino acid sequence of SEQ ID NO: 2, or variants thereof; or the amino acid sequence of SEQ ID NO: 2 and SEQ ID NO: 3, or variants thereof; for modulating movement of a L-type $Ca^{2+}$ channel $\beta_2$ subunit in a cardiac cell such as a myocyte in the heart of a subject.

In this respect, the invention also provides a method for modulating movement of a L-type $Ca^{2+}$ channel $\beta_2$ subunit in a cardiac cell such as a myocyte in the heart of a subject, comprising administering to the subject a peptide comprising: the amino acid sequence of SEQ ID NO: 2, or variants thereof; or SEQ ID NO: 2 and SEQ ID NO: 3, or variants thereof.

Binding of the peptide to the alpha-interacting domain can prevent movement of the $\beta_2$ subunit during activation and inactivation of the L-type $Ca^{2+}$ channel. Since the $\beta_2$ subunit is proposed to facilitate inactivation of the alpha subunit, this can result in a delay in inactivation of the current.

A subject that can be treated with a peptide of the invention will include humans as well as other mammals and animals.

In an aspect, the invention provides the use of a peptide comprising: the amino acid sequence of SEQ ID NO: 2, or variants thereof; or the amino acid sequence of SEQ ID NO: 2, and SEQ ID NO: 3, or variants thereof; for modulating a L-type $Ca^{2+}$ channel in a cardiac cell such as a myocyte in the heart of a subject.

In this respect, the invention also provides a method for modulating a L-type $Ca^{2+}$ channel in a cardiac cell such as a myocyte in the heart of a subject, comprising the step of administering to the subject a peptide comprising: the amino acid sequence of SEQ ID NO: 2, or variants thereof; or the amino acid sequence of SEQ ID NO: 2, and SEQ ID NO: 3, or variants thereof.

In another aspect, the invention provides the use of a peptide comprising: the amino acid sequence of SEQ ID NO: 2, or variants thereof; or the amino acid sequence of SEQ ID NO: 2, and SEQ ID NO: 3, or variants thereof; for preventing or reducing myocardial damage and/or oxidative stress in the heart of a subject.

In this respect, the invention also provides a method for preventing or reducing myocardial damage and/or oxidative stress in the heart of a subject, comprising the step of administering to the subject a peptide comprising: the amino acid sequence of SEQ ID NO: 2, or variants thereof; or the amino acid sequence of SEQ ID NO: 2, and SEQ ID NO: 3, or variants thereof.

The myocardial damage may include cardiac hypertrophy. Preferably, cardiac hypertrophy is reduced or prevented but intracellular $Ca^{2+}$ levels are reduced or substantially maintained in the heart of the subject. Substantially maintained indicates $Ca^{2+}$ levels which are the same or close to what is observed normally in the subject such as before cardiac hypertrophy.

The binding of a peptide of the invention to a L-type $Ca^{2+}$ channel results in a decrease of mitochondrial oxygen consumption or metabolism. As the peptide immobilizes the $\beta_2$ subunit, rather than the pore-forming $\alpha$1C subunit, this can occur without substantially altering calcium influx. Since this can occur at a concentration that does not alter calcium influx (1 $\mu$M), it may be a preferable agent to use in treating or preventing cardiac hypertrophy because any agent that decreases calcium influx may decrease contractility.

Thus, the invention provides uses and methods for the peptides of the invention as a treatment to prevent or reduce damage and/or oxidative stress in myocardial cells in a subject by modulating L-type $Ca^{2+}$ channel activity.

The peptides of the invention may be administered to treat or prevent cardiac hypertrophy in patients that have developed or are at risk of developing cardiac hypertrophy. The peptides of the invention can also be administered to reduce damage and/or oxidative stress to ischemic myocardial cells following a myocardial infarction in a subject during and after reperfusion therapy. The peptides may be administered before, after or during reperfusion.

In this respect, the invention also provides a use of a peptide comprising: the amino acid sequence of SEQ ID NO: 2; or the amino acid sequence of SEQ ID NO: 2, and SEQ ID NO: 3; in the preparation of a medicament for treating, preventing or ameliorating myocardial damage to a patient.

The invention also provides a use of a peptide comprising: the amino acid sequence of SEQ ID NO: 2, or variants thereof; or the amino acid sequence of SEQ ID NO: 2, and SEQ ID NO: 3, or variants thereof; in the manufacture of a medicament for treating, preventing or ameliorating myocardial damage to a patient, and/or oxidative stress in myocardial cells.

It may be preferable to administer the peptides of the invention in combination with other therapeutic agents that are useful for treating cardiac hypertrophy or HCM in a subject, or other agents which assist in reducing myocardial damage and/or oxidative stress. Such combinations could use conjugates comprising the peptides or the therapy could be concomitant or involve the sequential administration of the agents. Examples of such therapeutic agents may include, as some non-limiting examples, Antioxidants such as N-acetylcysteine, reduced glutathione, TAT-conjugated catalase or TAT-conjugated superoxide dismutase.

The peptides may be administered via a variety of methods, for example, as a therapeutic depending on the particular circumstances and as deemed appropriate by a medical practitioner.

In one non-limiting example, a peptide of the invention may be administered via the coronary arteries by a cardiologist/physician at the time of angiography or angioplasty in a hospital after admission with chest pain and diagnosis of coronary occlusion (myocardial infarction).

In another non-limiting example, a peptide of the invention may be administered to HCM patients prior to the development of cardiomyopathy. The peptide of the invention may be administered via intraperitoneal injection or via the coronary arteries to patients at risk of developing cardiomyopathy. Prevention of the development of cardiomyopathy may be measured by a decrease in intraventricular septal thickness or posterior wall thickness, and increase in left ventricular end diastolic dimension on echocardiography. The peptide of the invention may be administered about 3 times a week, on the basis that the half-life of the peptides of the invention in the body is likely to be approximately 3 to 4 days, consistent with the turnover rate of Cav1.2 channel protein (as described in Catalucci et al., *The Journal of Cell Biology* 184, 923-933 (2009)).

The effect of the administered therapeutic composition can be monitored by standard diagnostic procedures.

For example, effectiveness of the peptide may be monitored by echocardiography (ultrasound analysis of cardiac function) in one example. Size of damage could be assessed by release of muscle enzymes into the blood and by changes on electrocardiography (ECG).

Methods of Treatment

In yet another aspect, the present invention provides a method for modulating movement of a beta subunit of the L-type $Ca^{2+}$ channel in a cardiac cell in the heart of a subject, comprising administering to the subject a peptide comprising: the amino acid sequence of SEQ ID NO: 2; or the amino acid sequence of SEQ ID NO: 2, and SEQ ID NO: 3.

The present invention further provides a method for modulating binding of a beta subunit of the L-type $Ca^{2+}$ channel in a cardiac cell in the heart of a subject, comprising administering to the subject a peptide comprising: the amino acid sequence of SEQ ID NO: 2; or the amino acid sequence of SEQ ID NO: 2, and SEQ ID NO: 3. Preferably, the peptide prevents interaction between the beta subunit of the L-type $Ca^{2+}$ channel and an alpha subunit of the L-type $Ca^{2+}$ channel in a cardiac cell of a subject.

The present invention further provides a method for modulating a L-type $Ca^{2+}$ channel in a cardiac cell in the heart of a subject, comprising the step of administering to the subject a peptide comprising: the amino acid sequence of SEQ ID NO: 2, or variants thereof; or the amino acid sequence of SEQ ID NO: 2, and SEQ ID NO: 3, or variants thereof.

The present invention further provides a method for reducing myocardial damage and/or oxidative stress in the heart of a subject, comprising the step of administering to the subject a peptide comprising: the amino acid sequence of SEQ ID NO: 2, or variants thereof; or a peptide comprising the amino acid SEQ ID NO: 2, and SEQ ID NO: 3, or variants thereof.

The method of the invention may reduce cardiac hypertrophy but substantially maintain intracellular $Ca^{2+}$ levels in the heart of the subject.

Patients suffering from HCM present with elevated Um and mitochondrial metabolic activity, and a faster L-type $Ca^{2+}$ channel inactivation rate, even prior to the development of cardiomyopathy. Accordingly, the administration of the peptides of the invention, which can increase L-type $Ca^{2+}$ channel inactivation rate and decrease mitochondrial metabolic activity, can be used to prevent the development of cardiac hypertrophy in HCM patients.

Preferably, the method of treatment or use does not cause vasodilatory effects or negative inotropic effects as can occur with treatment with calcium channel antagonists.

In an aspect, the invention provides a method of preventing cardiac hypertrophy in the heart of a subject, comprising the step of administering to the subject a peptide comprising: the amino acid sequence of SEQ ID NO: 2, or variants thereof; or a peptide comprising the amino acid SEQ ID NO: 2, and SEQ ID NO: 3, or variants thereof. Preferably, the subject suffers from HCM.

In a further aspect, the invention provides a method or use for slowing the progression of myocardial fibrosis in a subject, comprising administering to the subject a peptide comprising: the amino acid sequence of SEQ ID NO: 2, or variants thereof; or a peptide comprising the amino acid SEQ ID NO: 2, and SEQ ID NO: 3, or variants thereof.

In a further aspect, the invention provides a method or use for modulating binding of a beta subunit of the L-type $Ca^{2+}$ channel in a cardiac cell of a subject, comprising administering to the subject a peptide of this invention, wherein the method is more effective at modulating the binding of a beta subunit of the L-type $Ca^{2+}$ channel in a cardiac cell of a subject compared to a method of administering QQLEEDLKGYLDWITQAE (SEQ ID NO:1).

In a further aspect, the invention provides a method or use for modulating a L-type $Ca^{2+}$ channel in a cardiac cell of a subject, comprising the step of administering to the subject a peptide of this invention, wherein the method is more effective at modulating the L-type $Ca^{2+}$ channel in a cardiac cell of a subject compared to a method of administering QQLEEDLKGYLDWITQAE (SEQ ID NO:1).

In a further aspect, the invention provides a method or use for reducing myocardial damage and/or oxidative stress in the heart of a subject, comprising the step of administering to the subject a peptide of this invention, wherein the method is more effective at reducing the myocardial damage and/or oxidative stress in the heart of a subject compared to a method of administering QQLEEDLKGYLDWITQAE (SEQ ID NO:1).

As used herein the term "subject" generally includes mammals such as: humans; farm animals such as sheep, goats, pigs, cows, horses, llamas; companion animals such as dogs and cats; primates; birds, such as chickens, geese and ducks; fish; and reptiles. The subject is preferably human.

Effective doses of the compositions of the present invention, for the treatment of the above described conditions vary depending upon many different factors, including means of administration, target site, physiological state of the patient, whether the patient is human or an animal, and other medications administered. Treatment dosages need to be titrated to optimize safety and efficacy.

The following Examples are to be construed as merely illustrative and not limitative of the remainder of the disclosure in any way whatsoever. These Examples are included solely for the purposes of exemplifying the present invention. They should not be understood as a restriction on the broad summary, disclosure or description of the invention as set out above. Without further elaboration, it is believed that one skilled in the art can, using the preceding description, utilize the present invention to its fullest extent. In the foregoing and in the following examples, all temperatures are set forth uncorrected in degrees Celsius; and, unless otherwise indicated, all parts and percentages are by weight.

EXAMPLES

Example 1—Synthesis of AID-Peptides

A peptide corresponding to the α1C-β2a interaction domain (AID) within the cytoplasmic I-II linker of the cardiac α1C subunit was synthesized by using the amino acid sequence, QQLEEDLKGYLDWITQAE (SEQ ID NO:1). A scrambled (inactive) control peptide (AID[S]) was also synthesized with the sequence, QKILGEWDLAQYTDQELE (SEQ ID NO: 10). Where required, a cell-penetrating TAT sequence was tethered to AID or AID (S) via 6-aminohexanoic acid (6-Ahx) (RKKRRQRRR) (SEQ ID NO: 3), to yield AID-TAT and AID(S)-TAT peptides.

Variant AID-peptides were also synthesised as listed in Table 4. Based on the original AID-TAT sequence, variant sequences were generated by truncating the amino end and/or carboxyl end of the original sequence or by inducing point mutations in amino acids.

TABLE 4

Variant AID-peptides.

| Peptide | Amino Acid Sequence | SEQ ID NO |
|---|---|---|
| Variant P1 | DLKGYLDWITQAE | SEQ ID NO: 11 |
| Variant P4 | LEEDLKGYLDWITQAE | SEQ ID NO: 12 |
| Variant P6 | KGYLDWITQAE | SEQ ID NO: 13 |
| Variant P7 | QQQEEDLKGYLDWITQAE | SEQ ID NO: 4 |
| Variant P10 | DLKGYLDWITQA | SEQ ID NO: 14 |
| Variant P11 | DLKGYLDWITQ | SEQ ID NO: 15 |
| Variant P12 | DLKGYLDWIT | SEQ ID NO: 16 |
| Variant P13 | QQLEEDLKGFLDAATQAE | SEQ ID NO: 17 |
| Variant P14 | QQEEEDLKGYLDWITQAE | SEQ ID NO: 5 |
| Variant P15 | QQEEEDEKGYLDWITQAE | SEQ ID NO: 6 |
| Variant P16 | QQREEDLKGYLDWITQAE | SEQ ID NO: 7 |

Example 2—Binding Assay-NHS Magnetic Beads

The affinity of each of the variant peptides to the $\beta_2$ subunit was investigated through binding competition assays.

PureProteome™ NHS FlexiBind Magnetic Beads (Cat. #LSKMAGN04, Merck) were used following manufacturer recommendations. Aminohexanoic acid linked AID peptide was bound to the NHS flexibind magnetic beads at a concentration of more than 2 mg/ml to obtain saturation of the beads with peptide. Beads were first primed with an equilibration buffer (1 mM HCL) to prepare them for binding. The Ahx-AID peptide was dissolved in wash/coupling buffer (PBS, pH 7.4) and added to the beads. The beads-AID peptide mixture was left to mix uniformly on a multiplate shaker at a speed of 300 rpm at room temperature for 2 hours. To reduce non-specific binding the beads were incubated in Quench Buffer (100 mM Tris-HCl, 150 mM NaCl, pH 8.0) at room temperature for 1 hour. After washing the cardiac lysate was added to increasing concentrations of the variant peptide to allow for competitive binding with the AID bound beads in the concentrations showed in Table 5.

TABLE 5

Sample preparation for pre-binding the AID/variant peptide to the $\beta_2$ subunit in whole heart lysate at varying concentrations.

| Final Peptide Concentration | Stock Peptide Concentration (μM) | Volume of stock peptide required in 200 μL (μL) | Volume of $\beta_2$ Lysate sample required in 200 μL (μL) | Volume of Wash/Coupling buffer required in 200 μL (μL) |
|---|---|---|---|---|
| 1 nM | 1 | 2 | 100 | 98 |
| 30 nM | 1 | 6 | 100 | 94 |
| 100 nM | 1 | 20 | 100 | 80 |
| 1 μM | 10 | 20 | 100 | 80 |
| 10 μM | 100 | 20 | 100 | 80 |

The AID-peptide bound beads were split into 5 aliquots for the 5 samples prepared in Table 5. The whole heart lysate added to each of the peptide-bound beads to allow competitive binding for 2 hours at room temperature.

Upon completion, the conjugate was washed in coupling buffer, to remove unbound fraction. SDS sample buffer was added to the beads, with the tubes then heated for 5 minutes at 95° C. The eluted sample stored at −20° C. to be run through sodium dodecyl sulfate-polyacrymalide gel electrophoresis (SDS-PAGE) to determine the binding affinity of each of the variants.

Example 3—Binding Assay-Streptavidin Beads

The use of streptavidin dynabeads and biotinylated peptide was developed to improve the binding affinity assays. The peptide was initially biotinylated using EZ-link amine-PEG11-biotin (Spacer arm: 53.2 Å, Thermofisher Scientific, Cat. #26136) which was dissolved in 0.1M MES buffer ((2-N-morpholino)-ethanesulfonic acid) at a concentration of 1 mM. Just prior to the reaction, 0.1M EDC (N-(3-Dimethylaminopropyl)-N'-ethylcarbodiimide hydrochloride) was dissolved in MES buffer. In order to achieve complete biotinylation of the AID peptide, a 50× molar excess of biotin to peptide was required, with the total volumes of each component required shown in Table 6.

TABLE 6

Volumes of each component required to achieve biotinylation of the AID peptide enough for one complete assay.

| | Amount/reaction (nM) | Stock conc (mM) | Volume/reaction (μl) | For dose-response curve (conc range: 0 nM-100 μM = 6 reactions) for each version of variant AID |
|---|---|---|---|---|
| AID | 0.02 | 0.1 | 0.2 | 1.2 μl |
| MES | | 100 | 9.8 | 58.8 μl |
| amine-$PEG_{11}$-biotin | 1 | 1 | 1 | 6 μl |
| EDC | 0.2 | 0.1 | 2 | 12 μl |
| Total | | | 13 | 78 μl |

Each 78 μL aliquot of the biotinylated peptide shown in Table 4 was enough for 6 reactions, covering the range of concentrations in which the heart lysate was again prepared with varying concentrations of the variant AID peptides according to Table 7.

TABLE 7

Sample preparation for pre-binding the AID/variant peptide to the $\beta_2$ subunit in whole heart lysate at varying concentrations.

| Final Peptide Concen-tration | Stock Peptide Concen-tration (μM) | Volume of stock peptide (μl) | Volume of heart lysate (μl) | PBS (μl) | Total (μl) |
|---|---|---|---|---|---|
| 0 | — | — | 15.4 | 34.6 | 50 |
| 10 nM | 0.1 | 5 | 15.4 | 29.6 | 50 |
| 100 nM | 1 | 5 | 15.4 | 29.6 | 50 |
| 1 μM | 10 | 5 | 15.4 | 29.6 | 50 |
| 10 μM | 100 | 5 | 15.4 | 29.6 | 50 |
| 100 μM | 1000 | 5 | 15.4 | 29.6 | 50 |

The 78 μL aliquot of biotinylated AID-peptide was mixed with streptavidin dynabeads (1 mg Dynabeads per every 200 μmol biotinylated peptide) for half an hour at room temperature. The heart lysate (100 Ig) was incubated with the variant peptides at room temperature for 2 hours. After removing all unbound peptide from the beads, they were mixed with the pre-bound heart lysate for 2 hours at room temperature. The unbound fraction was removed. The conjugate was heated at 95° C. for 5 minutes, with the sample buffer then eluted off and stored at −20° C. for SDS-PAGE analysis.

Example 4—Binding Affinity Analysis Using SDS-PAGE

SDS-PAGE was used to analyse all samples resulted from the binding affinity assays. 10 well Mini-Protean TGX Stain-Free Gels (Biorad) were loaded with 25 μL of each samples. A molecular weight ladder (Precision Protein Western C) was also loaded alongside the samples to be able to identify the presence of the β2 subunit (68 kDa). Gels were run in a Biorad electrophoresis tank powered by the PowerPac 3000 at constant current of 30 mA for 35 minutes. Upon completion, the gels were placed on nitrocellulose membrane to be transferred on the TransBlot Turbo for 3 minutes. The membranes were placed in blocking buffer (5% BSA) for 1 hour, before overnight incubation with Rabbit Anti-Cavβ2 polyclonal primary antibody (Alomone Labs #ACC-105) at 4° C. The membrane was washed three times for 10 minutes each with TBST before incubation with Goat Anti-Rabbit IgG (H+L)-HRP Conjugate secondary antibody (Abcam #ab97080, preabsorbed) in 5% BSA at room temperature for 1 hour. To visualize the protein bands Luminata Crescendo, Western HRP Substrate (Merck Millipore) and ChemiDoc imager (Biorad) with ImageLab software. Densitometric analysis performed using ImageJ software to quantify the intensity of the bands on the membrane corresponding to the Cavβ2.

Figure 2:
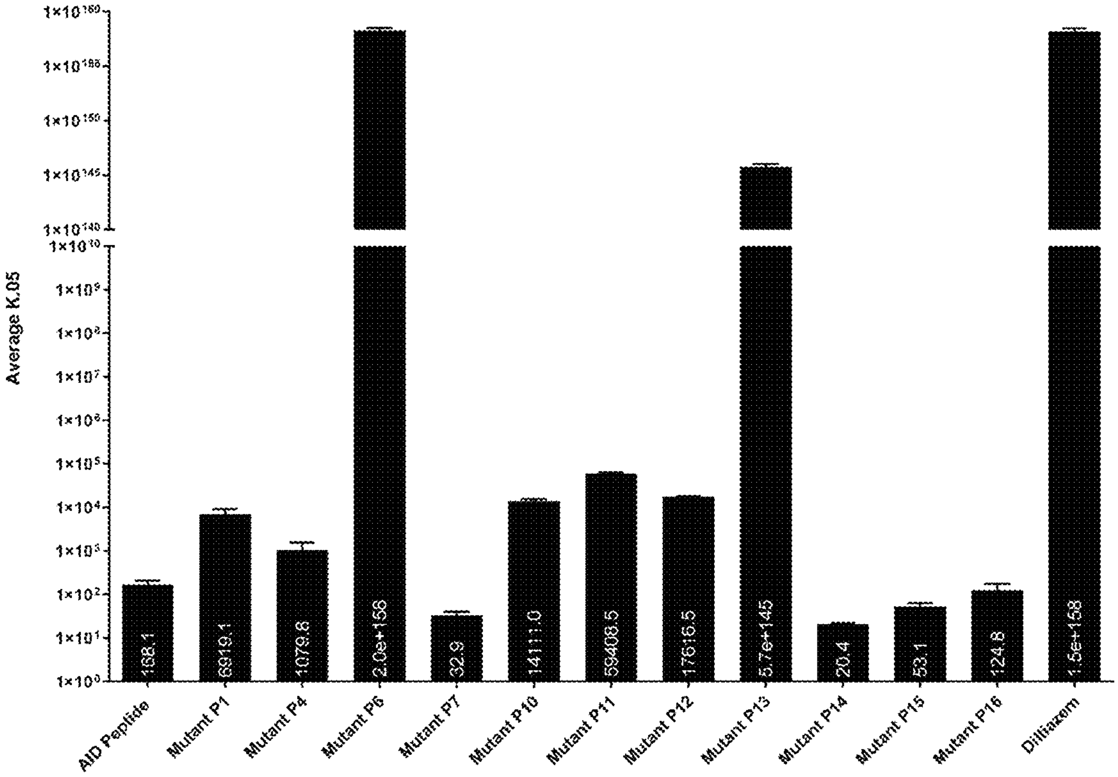
FIG. 2 presents the results of a competitive binding assay demonstrating mean binding affinity ($K_{0.5}$) of each mutant peptide, the full-length AID peptide and diltiazem for the $\beta$ subunit.

The average $K_{0.5}$ was calculated for each variant. These values are set out in FIG. 2, and the table below. Variants P7, P14, P15 and P16 demonstrated a greater binding affinity (lower $K_{0.5}$) for the target 32 subunit than the original AID peptide.

Example 5—Isolation of Adult Mouse Cardiac Myocytes

Adult male C57BL/6J mice were anesthetized with pentobarbitone sodium (240 mg/kg) via intraperitoneal injection prior to excision of the heart. Ventricular myocytes were isolated. Mouse hearts were cannulated onto a Langendorff apparatus via the aorta and perfused retrogradely with Krebs-Henseleit Buffer (KHB) containing (in mM): 120 NaCl, 25 $NaHCO_3$, 4.8 KCl, 2.2 $MgSO_4$, 1.2 $NaH_2PO_4$ and 11 glucose (pH=7.35 with O2/CO2 at 37° C.) for 4 min at 37° C. Hearts were then perfused with KHB supplemented with 2.4 mg/ml collagenase B for 3 min, then 8 min perfusion in the presence of 40 μM calcium. Following perfusion, aorta and atria were removed, and ventricles gently teased apart and triturated to dissociate myocytes into suspension. Myocyte suspension was centrifuged at 500 RPM for 3 min, supernatant discarded, and myocytes resuspended in calcium free HEPES-Buffered Solution (HBS) containing (in mM): 140 NaCl, 5.4 KCl, 0.5 $MgCl_2$, 5.5 HEPES, 11 glucose (pH=7.4 at 37° C.) in the presence or absence of 3 mM EGTA (for 0 mM calcium JC-1 experiments). For calcium containing (uptake) experiments, calcium was titrated back to achieve a final extracellular concentration of 2.0 mM.

Example 6—In Vitro Assessment of Cardiac Myocyte Function

All in vitro studies were performed in freshly isolated myocytes at 37° C. Fluorescence was recorded using a Hamamatsu Orca ER digital camera attached to an inverted Nikon TE2000-U microscope. Following a 20 min incubation with 0.5-1 μM AID(S)-TAT, AID-TAT, peptide 6 or peptide 7, fluorescent signal of individual myocytes was quantified using Metamorph 6.3 to measure signal intensity of manually traced cell regions. An equivalent region not containing cells was used for background and was subtracted.

Assessment of Intracellular Calcium Levels

Intracellular calcium was monitored in cardiac myocytes using the fluorescent indicator Fura-2 AM (Fura-2, 1 μM, ex 340/380 nm, em 510 nm, Molecular Probes). Oxidative stress was induced by applying a non-necrotic/non-apoptotic concentration of $H_2O_2$ (30 μm) to the myocytes for 5 min followed by 10 U/ml catalase. Fluorescence at 340/380 nm excitation and 510 nm emission were measured at 1 minute intervals with an exposure of 50 ms before and after exposure to 30 μM H2O2 (5 min) and 10 U/ml catalase (5 min). Ratiometric 340/380 nm signal was quantified and reported as a percentage from the baseline pre-treatment average.

The results are presented in FIG. 3(*a*). FIG. 3(*a*) demonstrates the effects of the peptides on an increase in intracellular calcium induced by a hydrogen peroxide insult ($H_2O_2$). Only P7 altered the increase in Fura 2 following $H_2O_2$. The mutant P7 was more effective at decreasing $H_2O_2$ induced increases in intracellular $Ca^{2+}$ (Fura 2) and superoxide production (DHE) than AID-TAT and had a similar effect on mitochondrial membrane potential (JC-1) as AID-TAT.

Assessment of Intracellular Superoxide Levels

Superoxide generation was assessed in cardiac myocytes using the fluorescent indicator dihydroethidium (DHE, 5 μM, 515-560 nm ex filter, 590 long pass em, Merck). Fluorescent images were taken at 1 min intervals with 200 ms exposure before and after exposure to 30 μM H2O2 (5 min) and 10 U/ml catalase (5 min). Fluorescence was reported as percentage change in the slope of the signal measured at 20-40 min (treatment) over 1-10 min (pre-treatment).

The results are presented in FIG. 3(*b*). Peptide 7 reduced the generation of superoxide in a statistically significant manner compared with peptide 6, AID-TAT, or AID(S)-TAT.

In Vitro Assessment of Mitochondrial Membrane Potential

Mitochondrial membrane potential (ψm) was monitored in cardiac myocytes by assessing alterations in 5,5',6,6'-tetrachloro-1,1',3,3'-tetraethylbenzimidazolylcarbocyanine iodide fluorescence (JC-1:200 nM, ex 480 nm, em 580/535 nm, Molecular Probes). Myocytes were incubated in calcium-free HBS (0 mM calcium, supplemented with 3 mM EGTA) for at least 3 h prior to measuring changes in $\Psi_m$. Fluorescent images were taken every 2 min before and after exposure to 30 μM $H_2O_2$ (5 min) and 10 U/ml catalase (5 min) (exposure=50 ms). Ratiometric 580/535 nm fluorescent signal was quantified and reported as a percentage from the baseline pre-treatment average. 40 mM NaCN was added at the end of each experiment to collapse $\Psi_m$, confirming that the JC-1 signal was indicative of $\Psi_m$.

The results are presented in FIG. 3(*c*). Only AID-TAT and peptide 7 reduced the mitochondrial membrane potential.

In Vitro Assessment of Mitochondrial Flavoprotein Oxidation

Autofluorescence was used to measure flavoprotein oxidation in cardiac myocytes based on previously described methods (480 nm ex, 535 nm em). Fluorescent images were taken at 1 min intervals with 1s exposure before and after exposure to L-type Ca2+ channel agonist BayK(−). Fluorescence was reported as a percentage from the baseline pre-treatment average.

Figure 4:
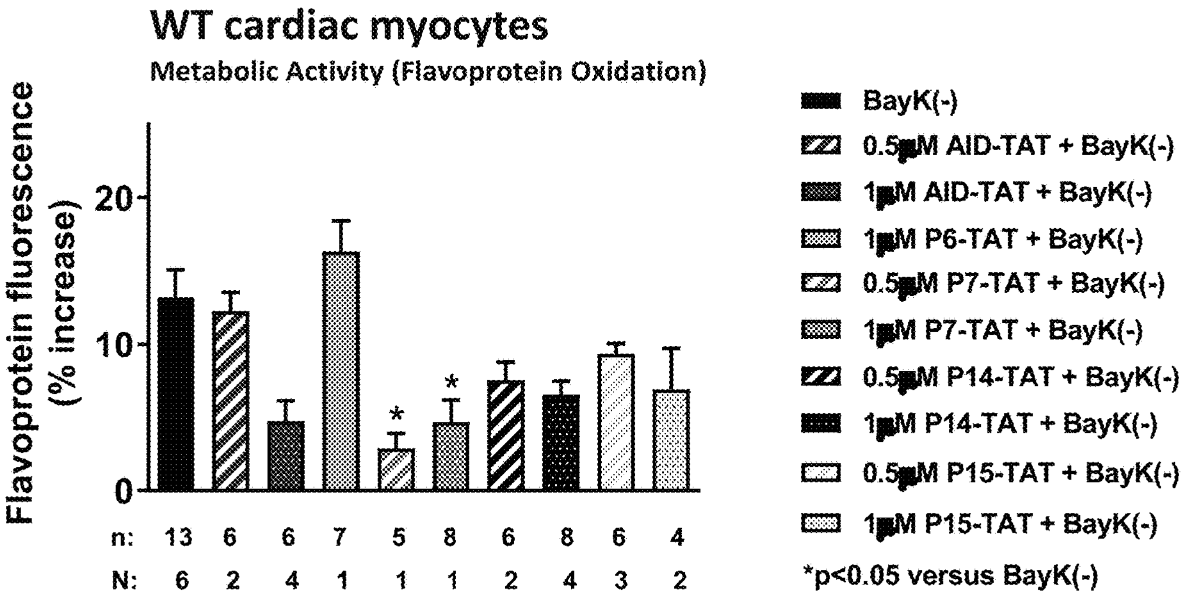
FIG. 4 presents the effect of mutant peptides on flavoprotein oxidation, a measure of metabolic activity and oxygen consumption in wt myocytes.
Figure 5:
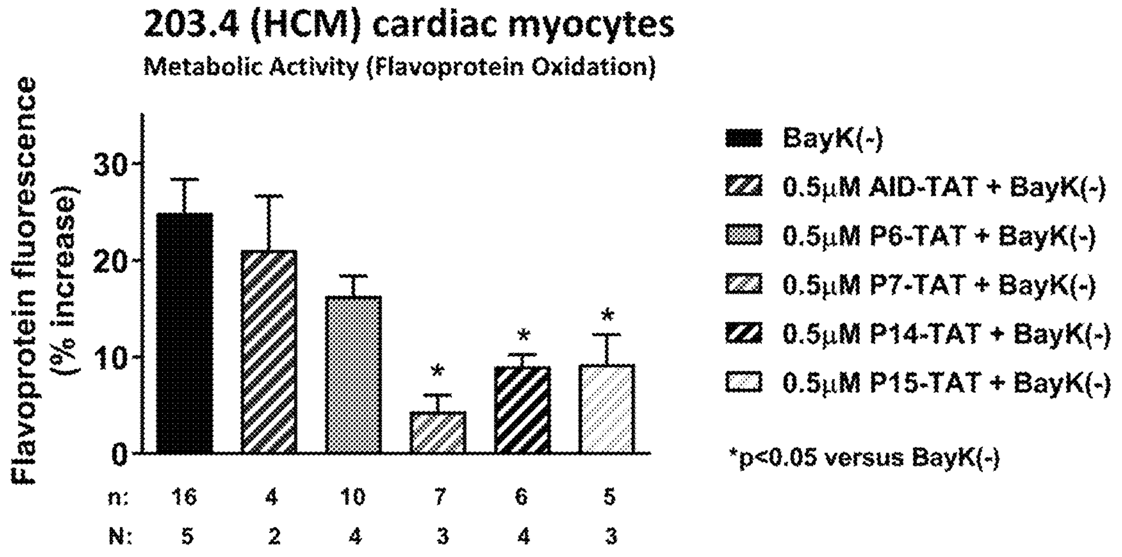
FIG. 5 presents the effect of mutant peptides on flavoprotein oxidation, a measure of metabolic activity and oxygen consumption in myocytes isolated from cTnI-G203S mutant mouse hearts that are hypertrophic.

The results from mutant peptides (P6-TAT, P7-TAT, P14-TAT and P15-TAT) and AID-TAT peptide are presented in FIG. 4 in wildtype cardiac myocytes and in FIG. 5 in myocytes from HCM hearts. The results show that P7, P14 and P15 presented a statistically significant reduction in flavoprotein oxidation in comparison with AID-TAT peptide in HCM hearts, and that P7 presented a statistically significant reduction in flavoprotein oxidation in comparison with AID-TAT peptide in wild type hearts.

Example 7—Assessment of Myocardial Ischemia-Reperfusion Injury

Adult male guinea pigs were anesthetized with pentobarbitone sodium (240 mg/kg) via intraperitoneal injection prior to excision of the heart. Guinea pig hearts were cannulated onto a Langendorff apparatus via the aorta and perfused retrogradely with $Ca^{2+}$ containing KHB comprising (in mM): 120 NaCl, 25 $NaHCO_3$, 4.8 KCl, 2.2 $MgSO_4$, 1.2 $NaH_2PO_4$, 11 glucose and 1.5 $CaCl_2$ (PH=7.35 with $O_2/CO_2$ at 37° C.) at 37° C. for 30 min at a rate of 7 mL/min, followed by 30 min no-flow ischemia, then 30 min reperfusion as previously described.

Perfusates were collected 20 and 25 min pre-ischemia and 20 and 30 min following reperfusion. A single dose of 0.5-10 μM AID(S)-TAT, AID-TAT, peptide 6 or peptide 7 was added to $Ca^{2+}$-containing KHB solution just prior to reperfusion. Creatine Kinase (CK) and Lactate Dehydrogenase (LDH) activity was measured in perfusates collected pre- and post-ischemia, and post-ischemia values normalized to pre-ischemia values.

For each sample, 10 μL of perfusate was added to 100 μL CK enzyme reagent (CK NAC-activated diagnostic kit, Randox Laboratories) and the rate of increase in absorbance recorded over 15 min at 30° C. using a spectrophotometer (PowerWave XS, BioTek, 340 nm). CK activity was calculated according to the equation:

$$CK\ \text{Activity}\ (\text{U/L}) = 4127 \times \left(\frac{\Delta A_{340\,nm}}{\text{min}}\right)$$

Figure 6A:
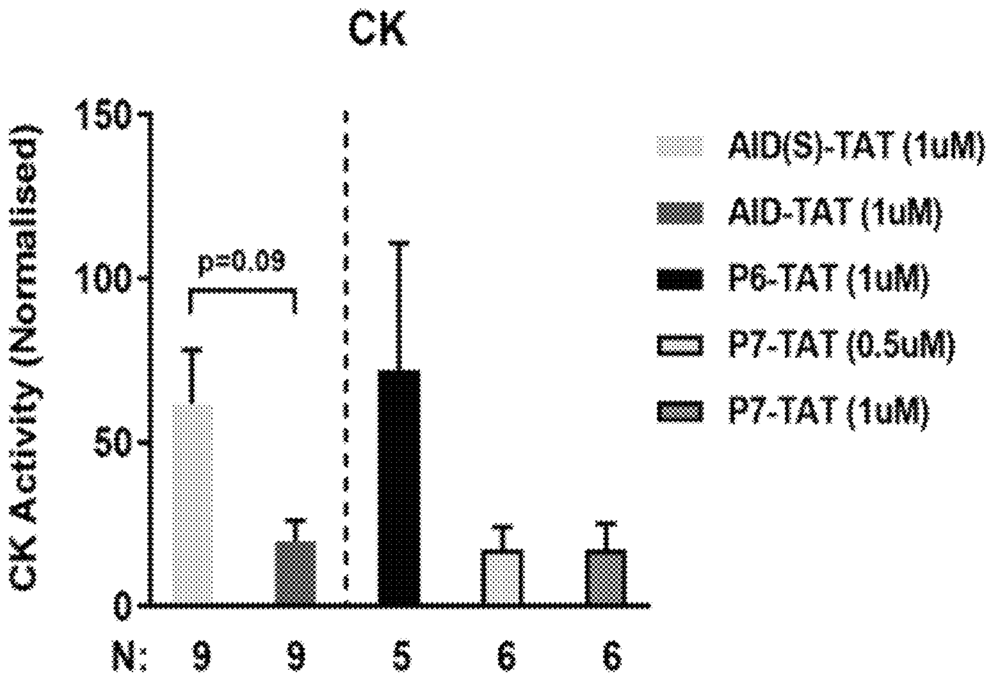
FIG. 6 presents the effect of mutant peptides on the release of CK and LDH (indication of necrosis), and oxidative stress measured as the ratio of reduced glutathione to oxidised glutathione (GSH:GSSG) in hearts exposed to no-flow ischemia for 20 min ex vivo.
Figure 6B:
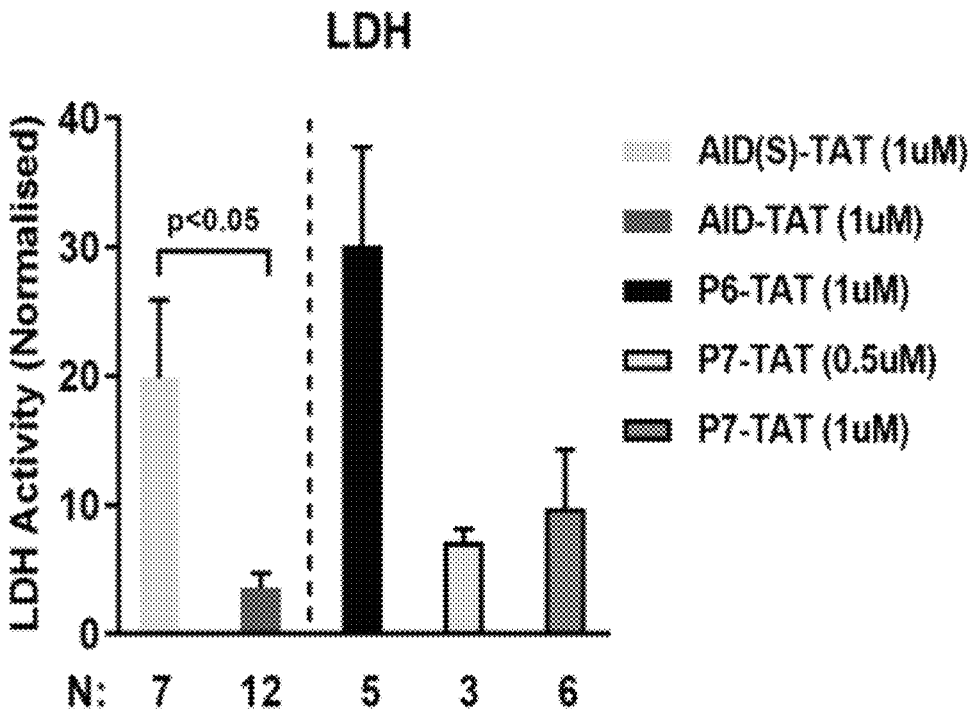
Figure 6C:
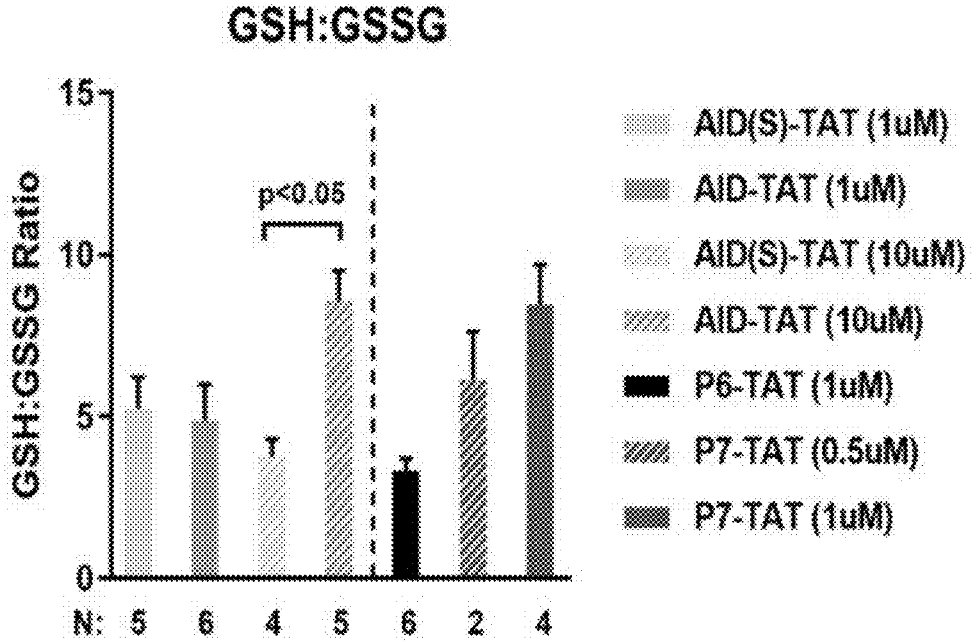

The results are presented in FIG. 6(*a*). CK activity was reduced compared to the AID(S)-TAT peptide in the AID-TAT, P7-TAT (1 μM) and P7-TAT (0.5 μM) samples. CK activity was reduced in both P7-TAT (1 μM) and P7-TAT (0.5 μM) compared to the P6-TAT peptide. P7-TAT (0.5 μM) was at least as effective as AID-TAT (1 μM).

To determine LDH activity, 150 μL of each sample was mixed with 50 μL of LDH reagent (50 mM imidazole buffer, 375 μM NADH, pyruvate and 0.05% BSA, pH=7) and the rate of decrease in absorbance recorded over 15 min at 25° C. using a spectrophotometer (PowerWave XS, BioTek, 340 nm). LDH activity was calculated according to the equation:

$$LDH\ \text{activity}\ (\text{U/mL}) = \frac{\frac{\Delta A_{340\,nm}}{\text{min}}(\text{Test}) - \frac{\Delta A_{340\,nm}}{\text{min}}(\text{Blank}) \times 3 \times (\text{dilution factor})}{6.22 \times 0.15}$$

The results are presented in FIG. 6(*b*). LDH was reduced compared to the AID(S)-TAT peptide in the AID-TAT, P7-TAT (1 μM) and P7-TAT (0.5 μM) samples. P7-TAT (0.5 μM) reduced LDH at least as well as AID-TAT (1 μM).

To determine GSH:GSSG, whole heart tissue was immediately homogenized following ischemia-reperfusion protocol, and GSH and GSSG levels assessed using a GSH/GSSG ratio detection assay kit as per manufacturer's instructions (abcam, ab205811).[8] Total glutathione and GSH were measured using a FLUOstar OPTIMA (BMG Labtech, ex 485-12 nm, em 520 nm). GSSG was calculated by subtracting GSH from total glutathione.

The results are presented in FIG. 6(*c*). AIDS-TAT samples at 1 μM did not show a statistically significant increase in the GSH:GSSG ratio, but AID-TAT samples at 10 μM did show a statistically significant increase in the GSH:GSSG ratio. P7-TAT samples at 1 μM and at 0.5 μM resulted in statistically significant increase in the GSH:GSSG ratio, comparable to the AID-TAT samples at 10 μM.

The reduction in CK activity, LDH activity and increase in GSH:GSSG ratio each represent a reduction in oxidative stress. The results demonstrate that the administration of P7-TAT reduced oxidative stress with reference to each of these markers. Further, P7-TAT was more effective than AID-TAT at reducing oxidative stress, with either superior results at the same concentration, or similar results with lower dosages of P7-TAT in comparison to AID-TAT.

Example 8—Prophylactic Administration of AID-TAT to cTnIG203S Mice

10 μM AID-TAT was administered to cTnIG203S mutant mice by intraperitoneal injection 3 times per week prior to the development of hypertrophic cardiomyopathy, for 5 weeks. The peptide was dissolved in phosphate buffered saline solution (PBS), and the total amount of the 10 μM AID-TAT administered over 5 weeks was 0.9 mg. Administration prevented the development of the hypertrophy as evidenced by a decrease in intraventricular septal thickness and increase in left ventricular end diastolic dimension on echocardiography. Fractional shortening also improved. The results are presented in FIG. 8. The AID-TAT peptide was administered 3 times per week because it was hypothesised that the bound AID-TAT peptide lasts 3-4 days, consistently with the turnover rate of the Cav1.2 channel protein.

Example 9—In Vitro Binding to the $I_{Ca-L}$ $\beta_2$ Subunit Demonstrates Increased Binding Affinity of $AID_{P7}$, $AID_{P14}$, $AID_{P15}$ and $AID_{P16}$ In this experiment, a binding affinity assay was utilized to examine the binding efficacy of AID peptide variants presented in Table 8, compared to the original AID peptide.

TABLE 8

| Peptide | Amino acid sequence |
|---|---|
| Original AID-TAT (full-length active) | QQLEEDLKGYLDWITQAE |
| AID(S)-TAT (scrambled inactive) | QKILGEWDLAQYTDQELE |
| $AID_{P1}$-TAT Mutant | DLKGYLDWITQAE |
| $AID_{P4}$-TAT Mutant | LEEDLKGYLDWITQAE |
| $AID_{P6}$-TAT Mutant | KGYLDWITQAE |
| $AID_{P7}$-TAT Mutant | QQ**Q**EEDLKGYLDWITQAE |
| $AID_{P10}$-TAT Mutant | DLKGYLDWITQA |
| $AID_{P11}$-TAT Mutant | DLKGYLDWITQ |
| $AID_{P12}$-TAT Mutant | DLKGYLDWIT |
| $AID_{P13}$-TAT Mutant | QQLEEDLKGFLD**AA**TQAE |
| $AID_{P14}$-TAT Mutant | QQ**E**EEDLKGYLDWITQAE |
| $AID_{P15}$-TAT Mutant | QQ**E**EED**E**KGYLDWITQAE |
| $AID_{P16}$-TAT Mutant | QQ**R**EEDLKGYLDWITQAE |

Biotinylation of original AID (no TAT): For each reaction (a dose-response curve consisted of 6 reactions), 0.02 nM AID-TAT was incubated in biotinylation solution (0.1M MES buffer containing 1 nM amine-$PEG_{11}$-biotin and 0.2 nM EDC) for 2 hrs at room temperature with agitation (400 rpm). Affinity beads (Dynabeads M-280 Streptavidin, ThermoFisher Scientific) were then incubated with biotinylated AID peptide for 30 min at room temperature with agitation (400 rpm). Afterwards, biotinylated AID-coated affinity beads were washed, initially in 0.1% BSA in PBS and then three times in PBS for 3 min.

Pre-binding AID (no TAT) mutant peptide of interest to Cavβ2 subunit: AID mutant peptides were serially diluted (0, 10 nM, 100 nM, 1 μM, 10 μM, 100 μM) and incubated with 100 μg of Cavβ2 subunit from cardiac homogenate and cytoplasmic protein preparation for 2 hrs at room temperature with agitation (400 rpm) as previously described (Haase H, Podzuweit T, Lutsch G, Hohaus A, Kostka S, Lindschau C, et al. Signaling from beta-adrenoceptor to L-type calcium channel: identification of a novel cardiac protein kinase A target possessing similarities to AHNAK. *FASEB J.* 1999; 13 (15): 2161-72; Hohaus A, Poteser M, Romanin C, Klugbauer N, Hofmann F, Morano I, et al. Modulation of the smooth-muscle L-type Ca2+ channel alpha1 subunit (alpha1C-b) by the beta2a subunit: a peptide which inhibits binding of beta to the I-II linker of alpha1 induces functional uncoupling. *Biochem J.* 2000; 348 Pt 3:657-65; Haase H, Striessnig J, Holtzhauer M, Vetter R, Glossmann H. A rapid procedure for the purification of cardiac 1,4-dihydropyridine receptors from porcine heart. *Eur J Pharmacol.* 1991; 207 (1): 51-9).

Competitive binding of AID-affinity beads and Cavβ2 subunit: Cavβ2-AID mutant peptide dilutions were then incubated with biotinylated AID-coated affinity beads for 2 hrs at room temperature with gentle agitation (400 rpm). Samples were placed on a magnetic stand to allow affinity beads to migrate to the magnet. Supernatant was removed and treated with 1× sample buffer (62.5 mM Tris-HCl, pH 6.8, 2% SDS, 10% glycerol, 100 mM DTT, 0.002% Bromophenol Blue) for 5 min at 95° C. Resulting protein was analysed by immunoblot.

Figure 9:
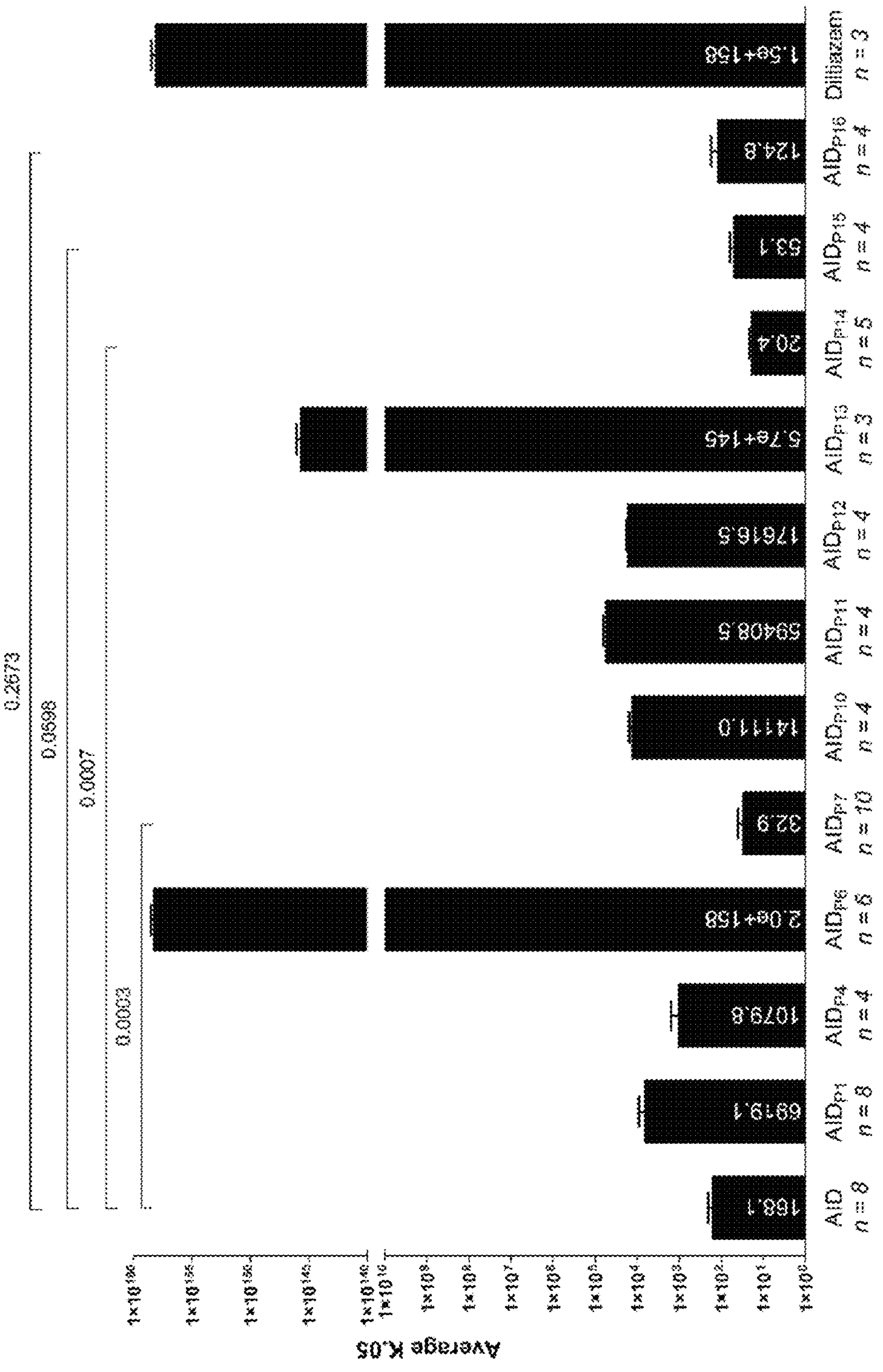
FIG. 9 presents the results of a competitive binding assay demonstrating mean binding affinity ($K_{0.5}$) of each mutant peptide, the full-length AID peptide and diltiazem for the $\beta$ subunit following exposure to 0, 10 nM, 100 nM, 1 μM, 10 μM and 100 μM of peptide.

Using a dose-response curve, decreased K0.5 values were found for $AID_{P7}$-TAT, $AID_{P14}$, $AID_{P15}$ and $AID_{P16}$ compared to AID peptide indicating a stronger binding affinity for these variants to the AID region (FIG. 9). In FIG. 9, n indicates number of technical replicates. P values shown compared with AID(S)-TAT as determined by the Mann-Whitney t-test. Further in vitro and in vivo experiments focussed on these 4 peptides.

Example 10—In Vitro Exposure of cTnI-G203S Cardiomyocytes to AID-TAT Variants are More Efficacious in Restoring $\psi_m$ and Flavoprotein Oxidation In this experiment wt myocytes were pre-exposed to 0.1, 0.5 or 1 μM for 20 min and assessed changes in flavoprotein oxidation and $\psi_m$.

Measurement of mitochondrial membrane potential: The fluorescent indicator 5,5',6,6'-tetrachloro1,1',3,3'-tetraethylbenzimidazolylcarbocyanine iodide (JC-1) was used to measure mitochondrial membrane potential (Um) as previously described (Viola H M, Arthur P G, Hool L C. Transient exposure to hydrogen peroxide causes an increase in mitochondria-derived superoxide as a result of sustained alteration in L-type Ca2+ channel function in the absence of apoptosis in ventricular myocytes. *Circ Res.* 2007; 100 (7): 1036-44). The fluorescence signal was measured on a Hamamatsu Orca ER digital camera attached to an inverted Nikon TE2000-U microscope. Images were acquired at 2 min intervals with 50 ms exposure. Metamorph 6.3 (Version 7.10.3) was used to quantify the signal by manually tracing myocytes. An equivalent region not containing cells was used as background and was subtracted. The 580 nm/535 nm ratiometric fluorescence values recorded over 6 min before and 4 min after addition of drugs were averaged and alterations in fluorescent ratios reported as the percentage increase from the basal average. To confirm that the signal was indicative of $\psi_m$, 40 mM NaCN was added at the end of each experiment to collapse Wm. In addition, individual 580 and 535 signals were assessed in each experiment to determine whether the fluorescent indicator was accurately measuring $\psi_m$. For calcium-free experiments, cells were exposed to calcium-free HBS (supplemented with 3 mM EGTA and 200 nM JC-1) for at least 3 h prior to measuring changes in $\psi_m$.

Measurement of mitochondrial flavoprotein oxidation: Flavoprotein autofluorescence was used to measure flavoprotein oxidation based on previously described methods (Yaniv Y, Juhaszova M, Lyashkov A E, Spurgeon H A, Sollott S J, Lakatta E G. Ca2+-regulated-cAMP/PKA signaling in cardiac pacemaker cells links ATP supply to demand. *J Mol Cell Cardiol.* 2011; 51 (5): 740-8). Fluorescence at excitation 480 nm and emission 535 nm was measured on a Hamamatsu Orca ER digital camera attached to an inverted Nikon TE2000-U microscope. Fluorescent images were acquired at 1 min intervals with 200 ms exposure. Metamorph 6.3 (Version 7.10.3) was used to quantify the signal by manually tracing myocytes. An equivalent region not containing cells was used as background and was subtracted. Fluorescence values recorded over 5 min before and 5 min after addition of drugs were averaged and alterations in fluorescent ratios reported as the percentage increase from the basal average. FCCP (50 μM) and NaCN (40 mM) was added at the end of each experiment to achieve a respective maximal and minimal fluorescence value indicative of maximal and minimal flavoprotein oxidation.

Figure 10A:
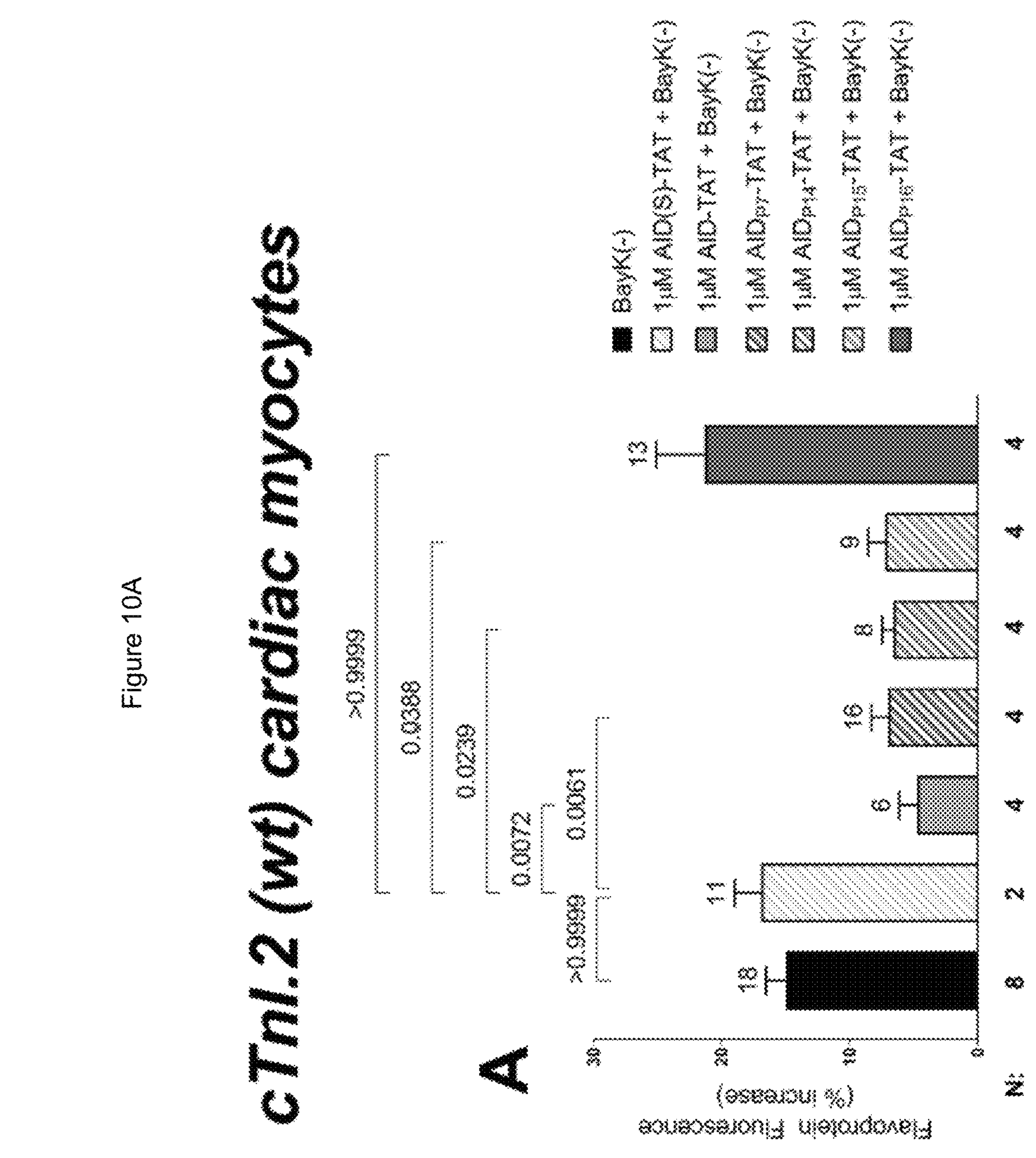
FIG. 10 illustrates that the in vitro exposure of cTnI.2 (wt) and cTnI-G203S (mutant) cardiomyocytes to variant peptides are more efficacious at restoring metabolic activity than original AID-TAT assessed as changes in flavoprotein oxidation.
Figure 10B:
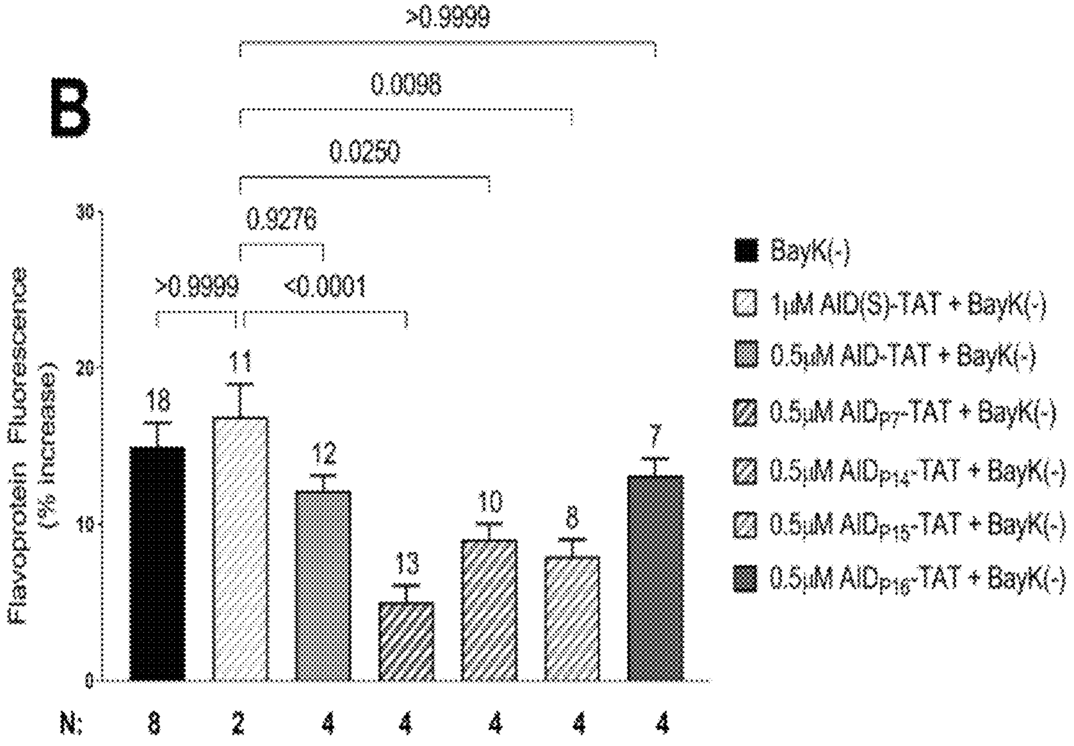
Figure 10C:
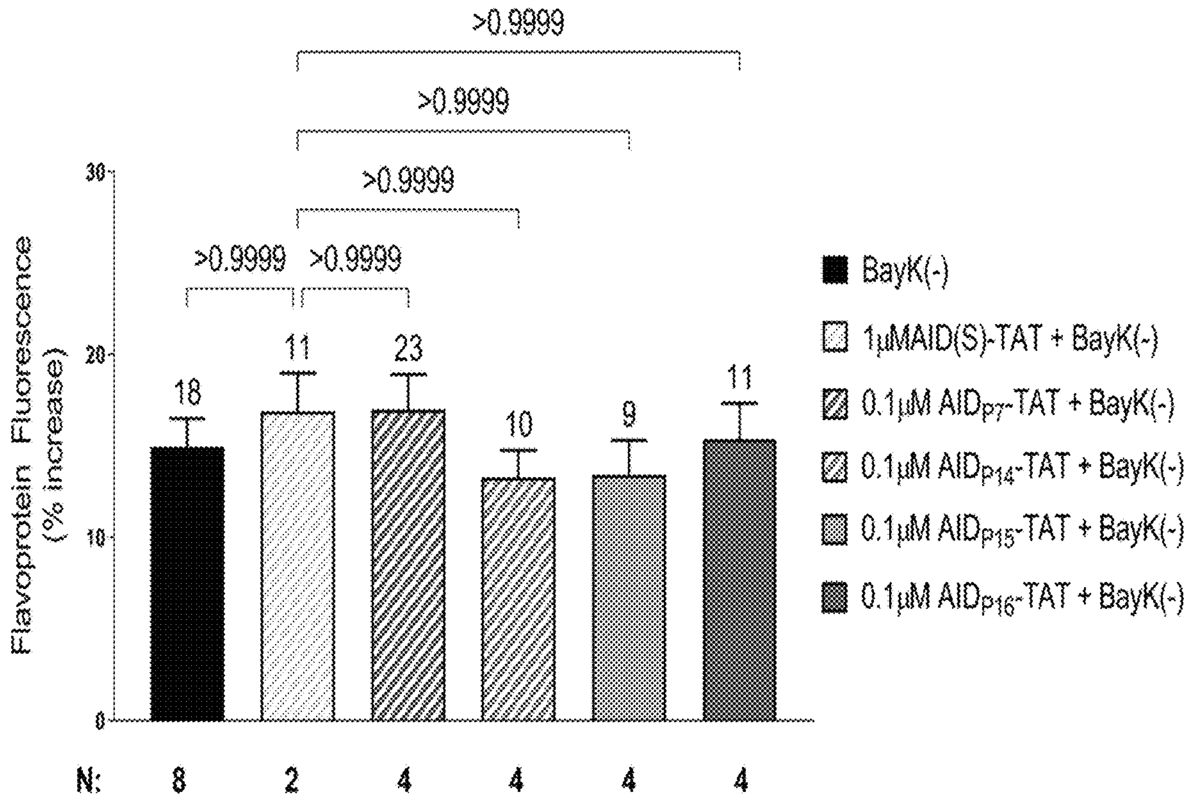
Figure 10D:
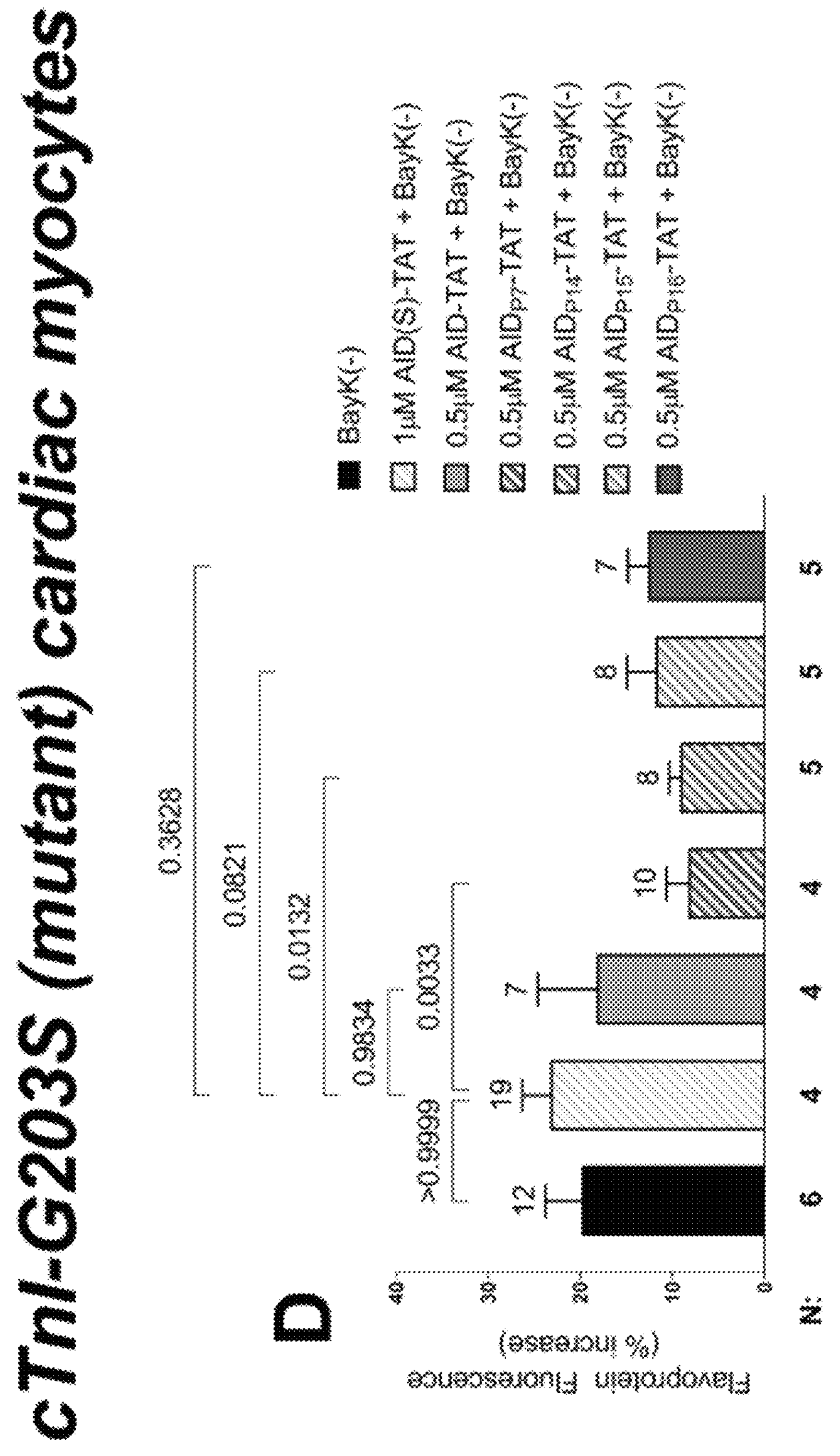

The $I_{ca-L}$ agonist BayK(−) was used to activate the channel and assess mitochondrial function. Consistent with previous findings, in the presence of 10 μM inactive scrambled peptide (AID(S)-TAT), BayK(−) induced an increase in flavoprotein oxidation that was comparable to the response elicited with application of BayK(−) alone (FIG. 10A-C) (Viola H M, Shah A A, Johnstone V P A, Cserne Szappanos H, Hodson M P, Hool L C. Characterization and validation of a preventative therapy for hypertrophic cardiomyopathy in a murine model of the disease. *Proc Natl Acad Sci USA.* 2020; 117 (37): 23113-24). Additionally, exposure of wt myocytes to 1 μM AID-TAT peptide was found to significantly attenuate the BayK(−) response (FIG. 10A). At 1 μM, peptide variants $AID_{P7}$-TAT, $AID_{P14}$-TAT and $AID_{P15}$-TAT were just as effective at attenuating the response in wt myocytes as the original AID-TAT (FIG. 10A). At a concentration of 0.5 μM, the original AID-TAT did not attenuate the response to BayK(−), whereas $AID_{P7}$-TAT, $AID_{P14}$ and $AID_{P15}$ were effective (P<0.05). At a concentration of 0.1 μM, neither the original AID-TAT peptide nor any of the AID-TAT peptide variants were effective (FIG. 10B-C). In cTnI-G203S myocytes, while 0.5 μM AID-TAT did not attenuate the response, $AID_{P7}$-TAT and $AID_{P14}$-TAT significantly attenuated increases in flavoprotein oxidation resulting from BayK(−) exposure (P<0.01 and P<0.05 respectively) (FIG. 10D). FIG. 10 presents the mean+/− SEM of flavoprotein fluorescence from cTnI.2 wt and cTnI-G203S mutant myocytes before and after exposure to 10 μM BayK(−) in the presence of 1 μM AID(S)-TAT, and increasing concentrations of variant peptides as indicated. N=no. of animals, n=no. of cardiomyocytes. P values shown compared with AID(S)-TAT as determined by the Kruskal-Wallis test.

Figure 11A:
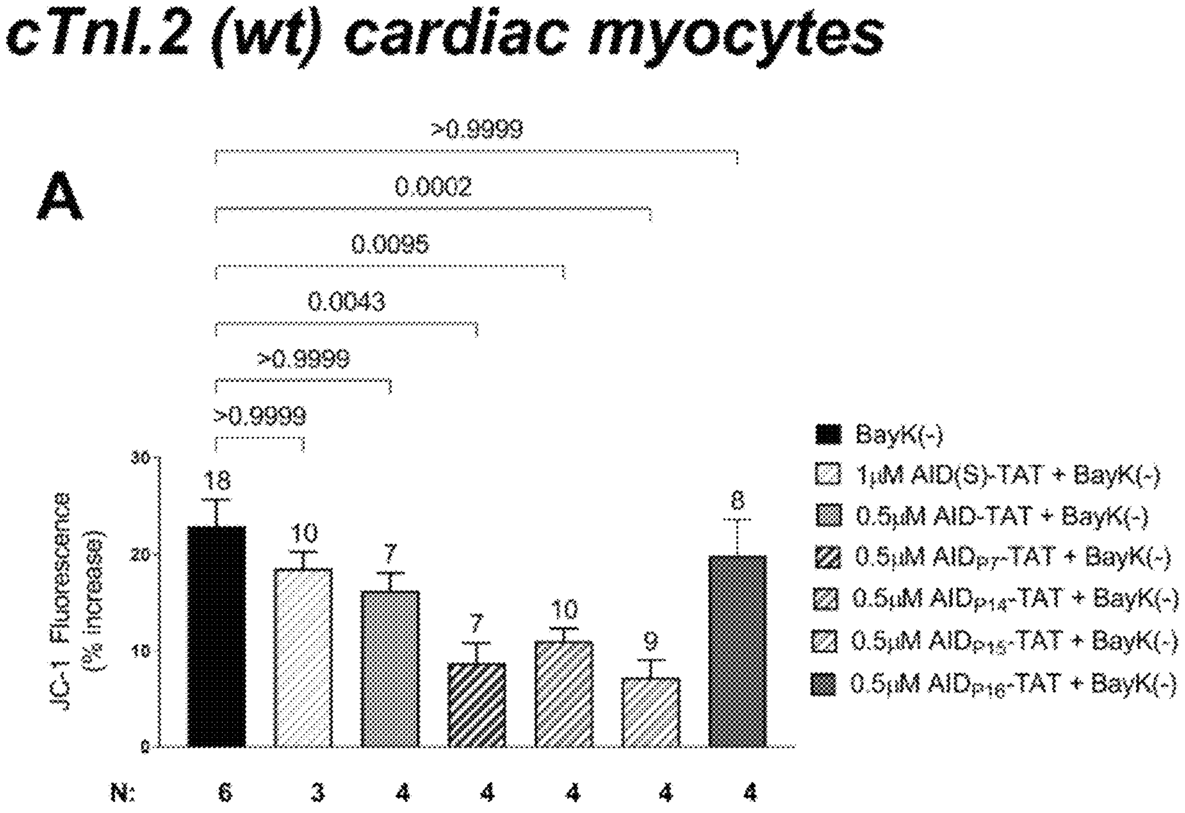
FIG. 11 illustrates that the in vitro exposure of cTnI.2 (wt) and cTnI-G203S (mutant) cardiomyocytes to variant peptides are more efficacious at restoring metabolic activity than original AID-TAT assessed as changes in JC-1 fluorescence.
Figure 11B:
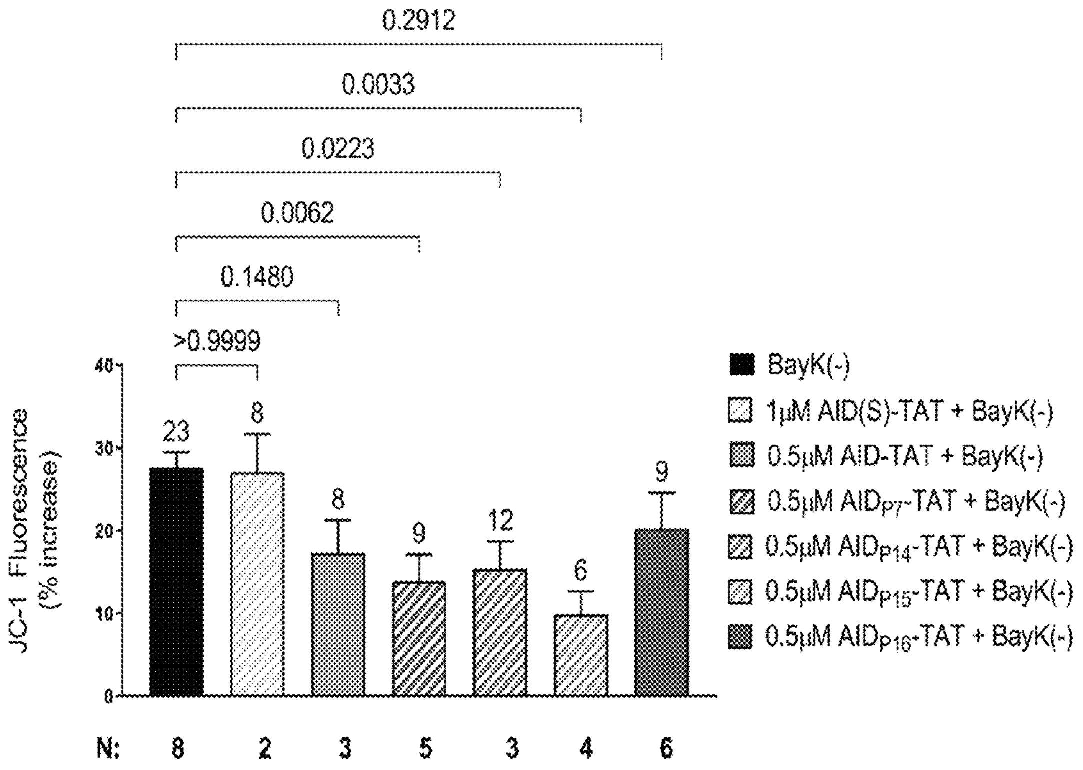

Based on results obtained from in vitro assessment of flavoprotein oxidation, the effect of 0.5 μM AID-TAT variants on changes in mitochondrial membrane potential ($\psi_m$) was further explored. Experiments were performed using JC-1 fluorescence under calcium-free conditions as previously described (Viola H, Johnstone V, Cserne Szappanos H, Richman T, Tsoutsman T, Filipovska A, et al. The L-type Ca (2+) channel facilitates abnormal metabolic activity in the cTnI-G203S mouse model of hypertrophic cardiomyopathy. J Physiol. 2016; 594 (14): 4051-70; Viola H M, Shah A A, Johnstone V P A, Cserne Szappanos H, Hodson M P, Hool L C. Characterization and validation of a preventative therapy for hypertrophic cardiomyopathy in a murine model of the disease. Proc Natl Acad Sci USA. 2020; 117 (37): 23113-24). Consistent with previous studies, application of BayK(−) induced an increase in $\psi_m$ in the presence of 10 μM AID(S)-TAT, that was comparable to BayK(−) alone, in both wt and cTnI-G203S myocytes (FIG. 11A-B). In both wt and cTnI-G203S myocytes, exposure to 0.5 μM AID-TAT was found not to be effective at attenuating the response to BayK(−), however, 0.5 μM $AID_{P7}$-TAT, $AID_{P14}$-TAT and $AID_{P15}$-TAT significantly attenuated the response (FIG. 11A-B). These data indicate that on an in vitro level, $AID_{P7}$-TAT and $AID_{P14}$-TAT are the most effective in normalising mitochondrial metabolic activity in cTnI-G203S myocytes. FIG. 11 presents the mean+/−SE of JC-1 fluorescence from cTnI.2 wt and cTnI-G203S mutant myocytes before and after exposure to 10 μM BayK(−) in the presence of 1 μM AID(S)-TAT, and 0.5 μM of variant peptides as indicated. N=no. of animals, n=no. of cardiomyocytes. P values shown compared with AID(S)-TAT as determined by the Kruskal-Wallis test.

Example 11—In Vivo Treatment of cTnI-G203S Mice with AID-TAT Variants does not Alter Blood Pressure Methods Twenty to thirty week-old male mice expressing the human cTnI gene encoding the human disease-causing cTnI-G203S were generated and used for the in vivo studies. By way of background, the mice develop hallmark features of HCM between 20 and 25 weeks (Viola H, Johnstone V, Cserne Szappanos H, Richman T, Tsoutsman T, Filipovska A, et al. The L-type Ca (2+) channel facilitates abnormal metabolic activity in the cTnI-G203S mouse model of hypertrophic cardiomyopathy. *J Physiol.* 2016; 594 (14): 4051-70; Viola H M, Shah A A, Johnstone V P A, Cserne Szappanos H, Hodson M P, Hool L C. Characterization and validation of a preventative therapy for hypertrophic cardiomyopathy in a murine model of the disease. *Proc Natl Acad Sci USA.* 2020; 117 (37): 23113-24; Tsoutsman T, Chung J, Doolan A, Nguyen L, Williams I A, Tu E, et al. Molecular insights from a novel cardiac troponin I mouse model of familial hypertrophic cardiomyopathy. *J Mol Cell Cardiol.* 2006; 41 (4): 623-32). Age-matched male mice expressing the normal human troponin I gene were used as controls and indicated as wild-type (wt). For in vivo studies, 20-week old cTnI-G203S mice were treated with 10 μM AID(S)-TAT (2 mg/kg) or 5 μM AID-TAT mutant peptides via intraperitoneal injection, 3 times per week for a total duration of 5 weeks. The peptide was dissolved in phosphate buffered saline solution (PBS), and the total amount of the 10 μM AID-TAT mutant peptides administered over 5 weeks was 0.9 mg. The total amount of the 5 μM AID-TAT mutant peptides administered over 5 weeks was 0.45 mg Male mice were utilized to eliminate potential differences in responses due to gender. The number of mice used is indicated by N.

Blood pressure was assessed prior to commencing the treatment regime, 1 hr after initial injection (acute) and following completion of the 5-week treatment regime. Blood pressure measurements of mice were obtained via the CODA non-invasive blood pressure system (Tail-Cuff Method, Kent Scientific Corporation). Conscious mice were placed into an appropriate size restrainer based on body weight and pre-set parameters to assess blood pressure (SOFTWARE details from Henrietta) were run for a total of 15 cycles (the first 5 cycles are undertaken for acclimatisation). An average of 10 measurements was used.

Results

Figure 12A:
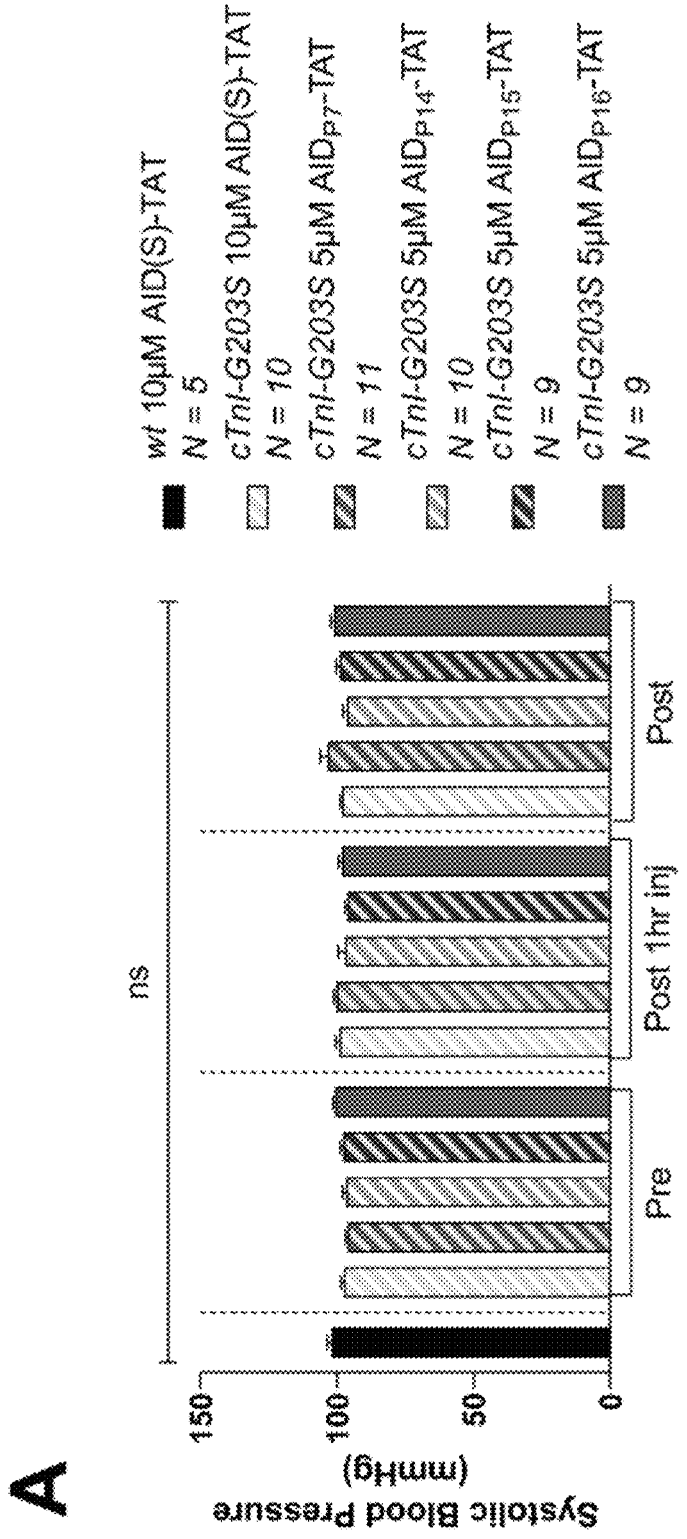
FIG. 12 illustrates that the in vivo treatment of cTnI-G203S (mutant) mice with AID-TAT variant peptides does not alter blood pressure.
Figure 12B:
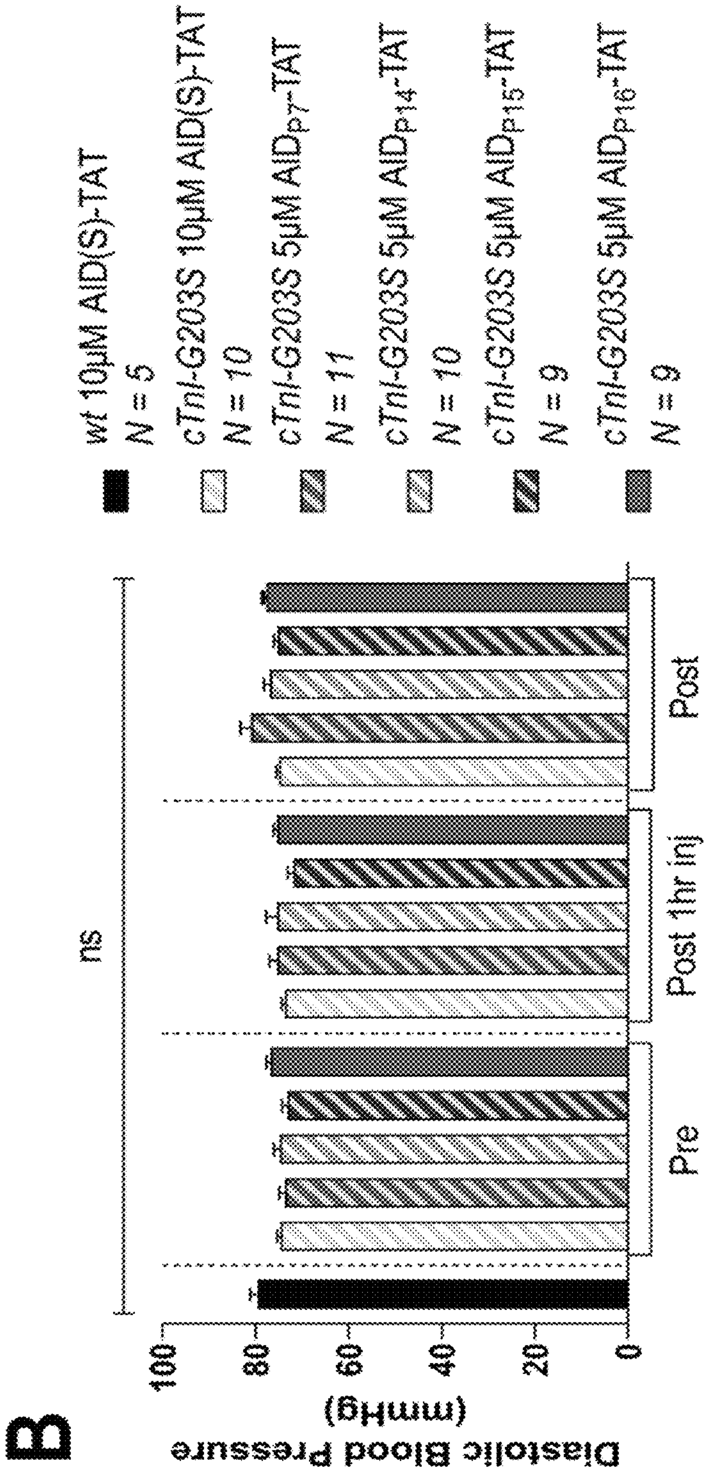

Systolic and diastolic blood pressures were recorded at 3 time points, including 1 hour before the first dose, 1 hr after the first dose (acute responses), and at the end of the 5-week treatment regime (chronic responses). No significant alterations in systolic or diastolic blood pressures were observed in mice treated with any of the AID-TAT variants at any time point (FIG. 12). These data indicate that the peptides do not cause vasodilatory effects or negative inotropic effects as can occur with treatment with calcium channel antagonists (eg Diltiazem). FIG. 12 presents the (A-B) mean±SEM of blood pressure measurements from wt and cTnI-G203S mice treated with 10 μM AID(S)-TAT, 5 μM $AID_{P7}$-TAT, 5 μM $AID_{P14}$-TAT, 5 μM $AID_{P15}$-TAT or 5 μM $AID_{P16}$-TAT (3×/wk/5 wk). Measurements were taken before start of treatment (Pre), 1 hr after initial injection (Post 1 hr inj.) or after 5-week treatment regime (Post) as indicated. N=number of mice as indicated. P=ns as determined by the Kruskal-Wallis test.

Example 12—In Vitro Toxicity

The fluorescent indicator propidium iodide (P4170; Sigma Aldrich) was used to assess AID-TAT mutant peptide toxicity in vitro in cardiac myocytes. Fluorescence at excitation 480 nm and emission 580 nm was measured on a Hamamatsu Orca ER digital camera attached to an inverted Nikon TE2000-U microscope. Fluorescent images were acquired after initial 20 min pre-incubation with 1 μM $AID_{P7}$-TAT (P7-TAT), $AID_{P14}$-TAT (P14-TAT), $AID_{P15}$-TAT (P15-TAT), or $AID_{P16}$-TAT (P16-TAT), and after 5 min incubation with the dye, using 50 ms exposure. No evidence of toxicity was observed.

Example 13—In Vivo Treatment of cTnI-G203S Mice with AID-TAT Variants is not Toxic In Vivo Toxicity Parameters Mice were treated with 5 μM AID(S)-TAT, $AID_{P7}$-TAT (P7-TAT), $AID_{P14}$-TAT (P14-TAT) or $AID_{P15}$-TAT (P15-TAT) or $AID_{P16}$-TAT 3×/wk/5 wk (equalling 15 doses). The peptide was dissolved in phosphate buffered saline solution (PBS), and the total amount of the 5 μM AID-TAT mutant peptides administered over 5 weeks was 0.45 mg. Body weight was recorded prior to administration of each peptide dose. A 5-10% reduction in weight may indicate toxicity and warrants additional monitoring as recommended by The Animal Ethics Committee of the University of Western Australia in accordance with the Guidelines to Promote the Wellbeing of Animals Used for Scientific Purposes (NHMRC 2008). Following completion of the treatment regime, mice were anesthetised and terminal blood collected. Blood was left to coagulate in a Lithium-Heparin tube at room temperature for 20 min. Plasma was separated using centrifugation at 3000 g for 10 min at 4° C. To measure kidney toxicity, urea and creatinine concentrations were assessed using Quantichrom Urea assay kit (BioAssay Systems, Hayward, CA) and Quantichrom Creatinine assay kit (BioAssay Systems, Hayward, CA), respectively. To measure liver toxicity, alanine transaminase (ALT) and aspartate transaminase (AST) concentrations were measured using Alanine Transaminase assay kit (BioAssay Systems, Hayward, CA) and Aspartate Transaminase assay kit (BioAssay Systems, Hayward, CA), respectively. Assays were performed as per manufacturer's instructions, using a spectrophotometer (CLARIOstar, BMG LABTECH).

Results

Figure 13A:
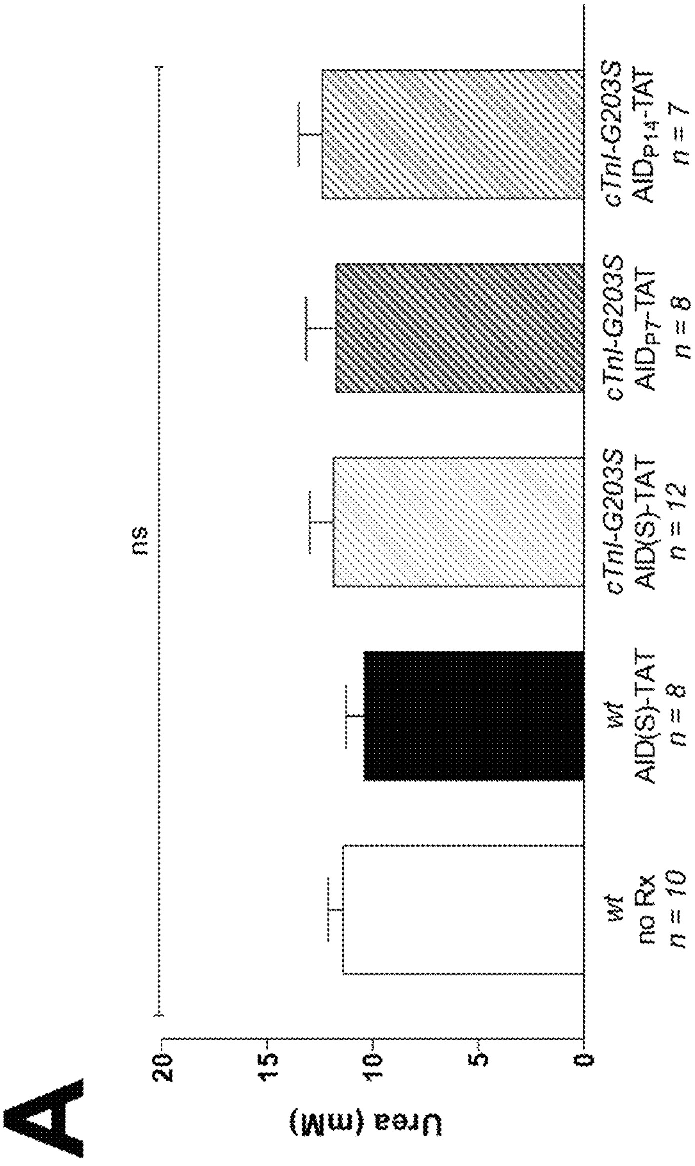
FIG. 13 illustrates that the in vivo treatment of cTnI-G203S mice with AID-TAT variant peptides are not toxic.
Figure 13B:
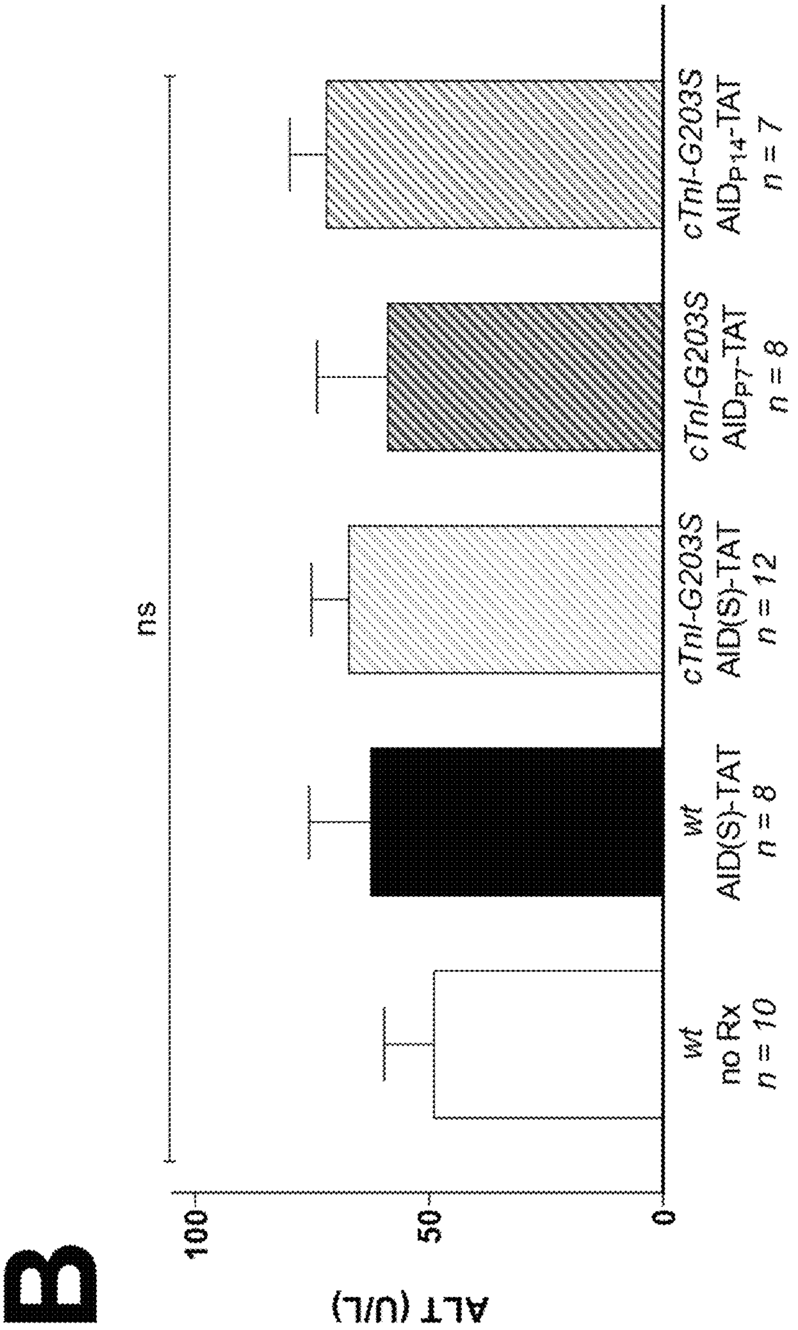
Figure 13C:
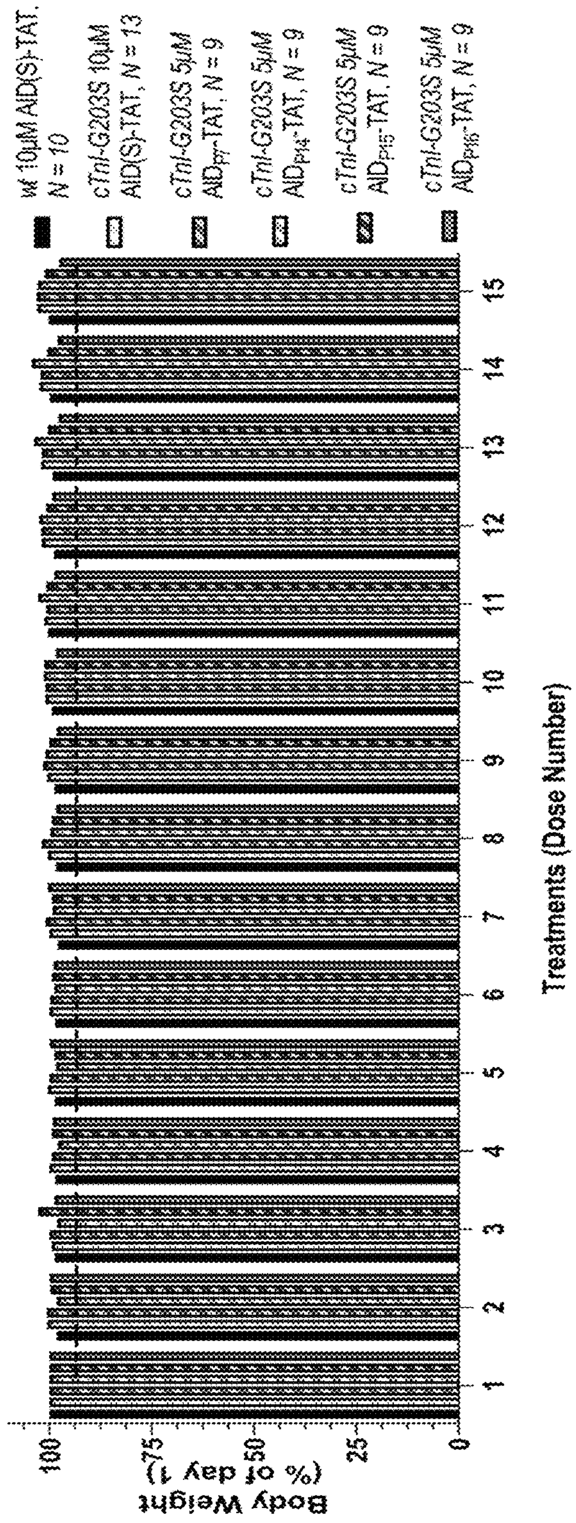

Following completion of the 5-week in vivo treatment regime, terminal plasma was collected and assessed for kidney and liver toxicity. No significant alterations in urea, or alanine transaminase (ALT) were observed compared to plasma assessed from AID(S)-TAT-treated wt and cTnI-G203S mice, indicating treatment with AID-TAT variants does not cause kidney or liver toxicity (FIG. 13A-B). Additionally, no significant reduction in body weight was observed over the duration of all treatment protocols (FIG. 13C). Overall, these data indicate that in vivo treatment of cTnI-G203S mice with AID-TAT variants is not toxic. FIG. 13 presents the mean±SEM of urea (A) and ALT (B) concentrations from plasma from wt and cTnI-G203S mice treated with 10 μM AID(S)-TAT, 5 μM $AID_{P7}$-TAT or 5 μM $AID_{P14}$-TAT or $AID_{P15}$-TAT or $AID_{P16}$-TAT (3×/wk/5 wk) as indicated. N=number of mice. P=ns as determined by ANOVA and Kruskal-Wallis tests (A-B). (C) Mean+ SEM of body weight recorded from cTnI-G203S mice treated with 5 μM AID(S)-TAT, 5 μM $AID_{P7}$-TAT, 5 μM $AID_{P14}$-TAT, 5 μM $AID_{P15}$-TAT or 5 μM $AID_{P16}$-TAT (3×/wk/5 wk, equalling 15 doses in total) as indicated. N=number of mice as indicated. Red line denotes 5% weight loss threshold.

Example 14—In Vivo Treatment of Pre-Cardiomyopathic cTnI-G203S Mice with AID-TAT Variants Slows the Progression of Fibrosis Methods Following completion of treatment regimes, mouse hearts were extracted and prepared for Masson's Trichchrome staining based on previously described methods with minor modifications (Van De Vlekkert D, Machado E, d'Azzo A. Analysis of Generalized Fibrosis in Mouse Tissue Sections with Masson's Trichrome Staining. *Bio Protoc.* 2020; 10 (10): e3629). Hearts were washed in PBS and fixed overnight in 10% buffered formalin saline (FSAL-5L; Hurst Scientific, AUS). After fixation, hearts were washed 3×10 min in PBS and incubated overnight in 30% sucrose solution (in PBS). After overnight incubation, hearts were then coated in Tissue-Tek OCT compound (IA018; ProSciTech, AUS) and embedded into 4 cm-deep cylindrical alfoil moulds containing ~2 ml OCT. The moulds were lowered into an Isopentane-filled tube in a liquid nitrogen-containing canister to allow slow freezing of the heart tissue. Tissue samples were stored at −80° C. until cryosectioning.

Hearts were cut into 7 μM sections and collected on warm (RT) subbed Superfrost slides and stored at −80° C. until staining.

To achieve thermal equilibration prior to Masson's trichrome staining, slides were transferred from −80° C. to −20° C. overnight. After overnight incubation, slides were transferred from −20° C. to RT for 1 hr before 1×2 min wash in running tap H2O to remove OCT and secondary fixation in Bouin's solution overnight. Slides were washed 1-3×5 min in running $H_2O$ for complete removal of Bouin's solution. Slides were stained using the following steps: Celestine Blue (5 min), running tap $H_2O$ (2 min), Harris Hemotoxylin (5 min), running tap $H_2O$ (2 min), distilled $H_2O$ (2 min), Ponceau-Fuchsin (10 mins), distilled $H_2O$ (20 sec), Phosphomolybdic acid (4 min), Aniline Blue (1 min) and 1% acetic acid (1 min). Slides were then blot dried with filter paper and dehydration, clearing and mounting steps were done as previously outlined (Van De Vlekkert D, Machado E, d'Azzo A. Analysis of Generalized Fibrosis in Mouse Tissue Sections with Masson's Trichrome Staining. Bio Protoc. 2020; 10 (10): e3629).

To observe the levels of cardiac fibrosis in mice, a minimum of 15 sections of microscopic fields for each animal were selected randomly for histological analysis. Images of heart sections were obtained using a Nikon upright light microscope (DS-Qi2, Japan) at 20× magnification and analysed using ImageJ (NIH). The ratio of blue area to the total myocardium area in Masson's trichrome-stained sections was used to analyse collagen accumulation. Two researchers blindly performed analyses of histological features.

Results

It is well-established that myocardial fibrosis is a characteristic feature of HCM (O'Connell T D, Rodrigo M C, Simpson P C. Isolation and culture of adult mouse cardiac myocytes. *Methods Mol Biol.* 2007; 357:271-96). Myocardial fibrosis is the collagen-rich extracellular matrix that is significantly increased in hypertrophic hearts (Haase H, Striessnig J, Holtzhauer M, Vetter R, Glossmann H. A rapid procedure for the purification of cardiac 1,4-dihydropyridine receptors from porcine heart. Eur J Pharmacol. 1991; 207 (1): 51-9). Increased collagen accumulation and fibrosis is maladaptive and is associated with impaired cardiac relaxation, thereby increasing the risk of heart failure (Tang H, Viola H M, Filipovska A, Hool L C. Ca (v) 1.2 calcium channel is glutathionylated during oxidative stress in guinea pig and ischemic human heart. *Free Radic Biol Med.* 2011; 51 (8): 1501-11).

Figure 14A:
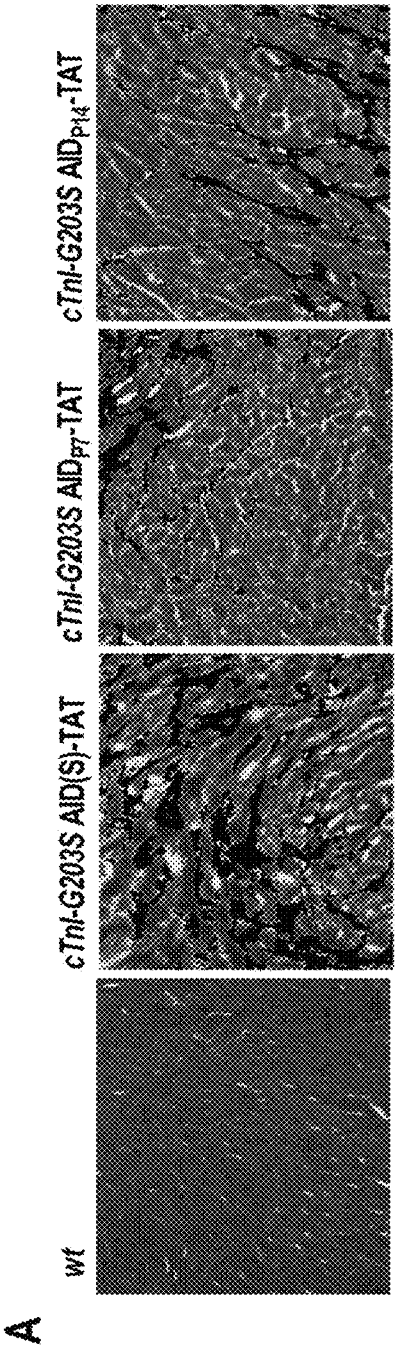
FIG. 14 illustrates that the in vivo treatment of cTnI-G203S mice with AID-TAT variant peptides slows the progression of fibrosis.
Figure 14B:
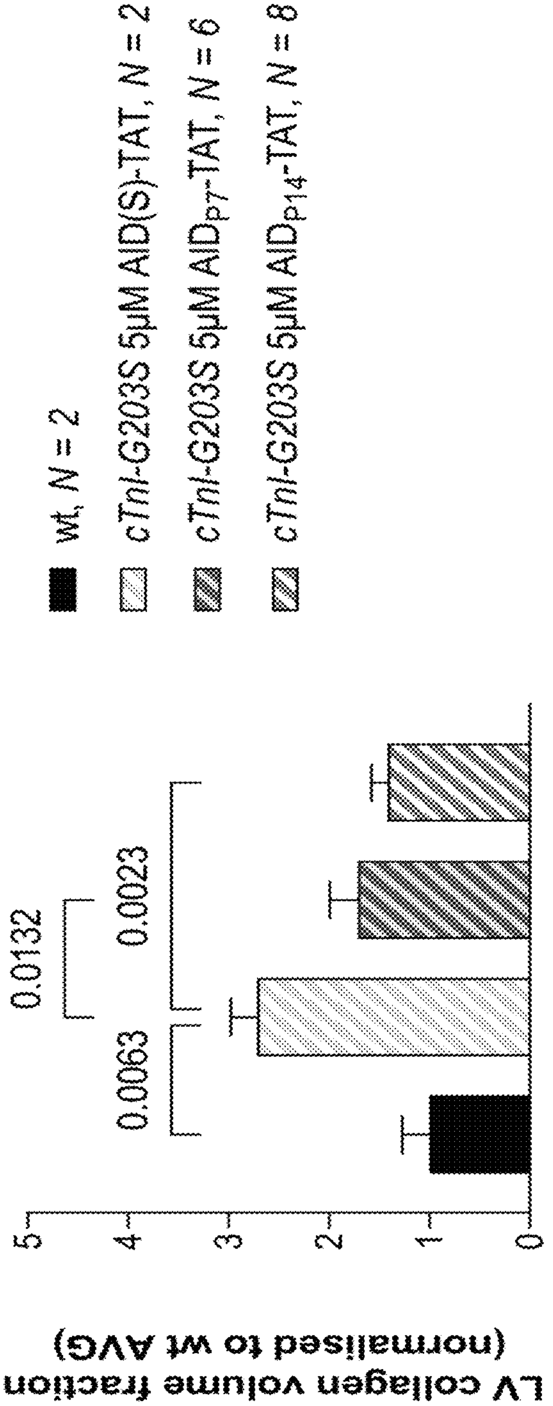

Here we assessed the efficacy of treating 20-week-old pre-hypertrophic cTnI-G203S mice with 5 μM AID-TAT variant peptides (3×/wk/5 wk) on the development and progression of fibrosis. The peptide was dissolved in phosphate buffered saline solution (PBS), and the total amount of the 5 μM AID-TAT variant peptides administered over 5 weeks was 0.45 mg. Following the 5-week treatment regime, murine hearts were extracted, fixed, and embedded in OCT for cryosectioning. The collagen deposition in cardiac tissue sections was visualised using Masson's Trichrome staining indicating muscle tissue (stained red), nuclei (stained purple/black) and collagen (stained blue). Images were acquired using a Nikon Upright Microscope and collagen volume fraction (%) was determined using ImageJ colour thresholding. Consistent with the development of HCM, we found that left ventricular posterior wall collagen volume fraction (CVF, %) was significantly increased in cTnI-G203S mice treated with 10 μM AID(S)-TAT versus wt myocytes (FIG. 14). This was significantly decreased, in cTnI-G203S mice treated with 5 μM $AID_{P7}$-TAT (P7-TAT) (FIG. 14). FIG. 14 presents: (A) Representative sections of left ventricular cardiac tissue. Scale bar=50 μM. (B) LV collagen volume fraction (%) from sectioned hearts of 25 week old wt and 25 week old cTnI-G203S mice following treatment with 10 μM AID(S)-TAT, 5 μM $AID_{P7}$-TAT or 5 μM $AID_{P14}$-TAT (3×/wk/5 wk). N=number of mice as indicated. Values reported as mean±SEM; P values compared with cTnI-G203S AID(S)-TAT as determined by the Kruskal-Wallis test.

Example 15—In Vivo Treatment of Pre-Cardiomyopathic cTnI-G203S Mice with AID Peptide Variants Prevents the Development of Hypertrophic Cardiomyopathy Methods Echocardiographic studies to measure left ventricular function were performed on mice under light methoxyflurane anaesthesia with the use of an i13L probe on a Vivid™ 7 IQ ultrasound system (GE Healthcare, Little Chalfont, UK) as previously described (Viola H, Johnstone V, Cserne Szappanos H, Richman T, Tsoutsman T, Filipovska A, et al. The L-type Ca(2+) channel facilitates abnormal metabolic activity in the cTnI-G203S mouse model of hypertrophic cardiomyopathy. *J Physiol.* 2016; 594 (14): 4051-70; Viola H M, Shah A A, Johnstone V P A, Cserne Szappanos H, Hodson M P, Hool L C. Characterization and validation of a preventative therapy for hypertrophic cardiomyopathy in a murine model of the disease. *Proc Natl Acad Sci USA.* 2020; 117 (37): 23113-24; Viola H M, Johnstone V P A, Cserne Szappanos H, Richman T R, Tsoutsman T, Filipovska A, et al. The Role of the L-Type Ca (2+) Channel in Altered Metabolic Activity in a Murine Model of Hypertrophic Cardiomyopathy. *JACC Basic Transl Sci.* 2016; 1 (1-2): 61-72). Each N represents the average of quantitative measurements from wt or cTnI-G203S mice for each treatment group.

Results

Figure 15:
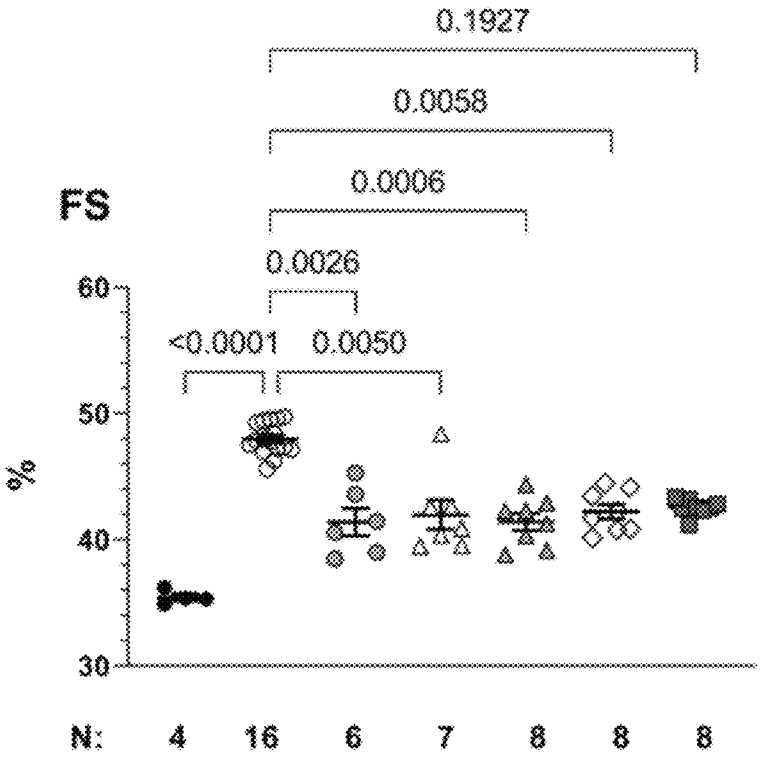
FIG. 15 illustrates the echocardiographic parameters of mice exposed to 10 μM AID(S), 10 μM AID-TAT, 5 μM $AID_{P7}$-TAT, 5 μM $AID_{P14}$-TAT, 5 μM $AID_{P15}$-TAT or 5 μM $AID_{P16}$-TAT.
Figure 15:
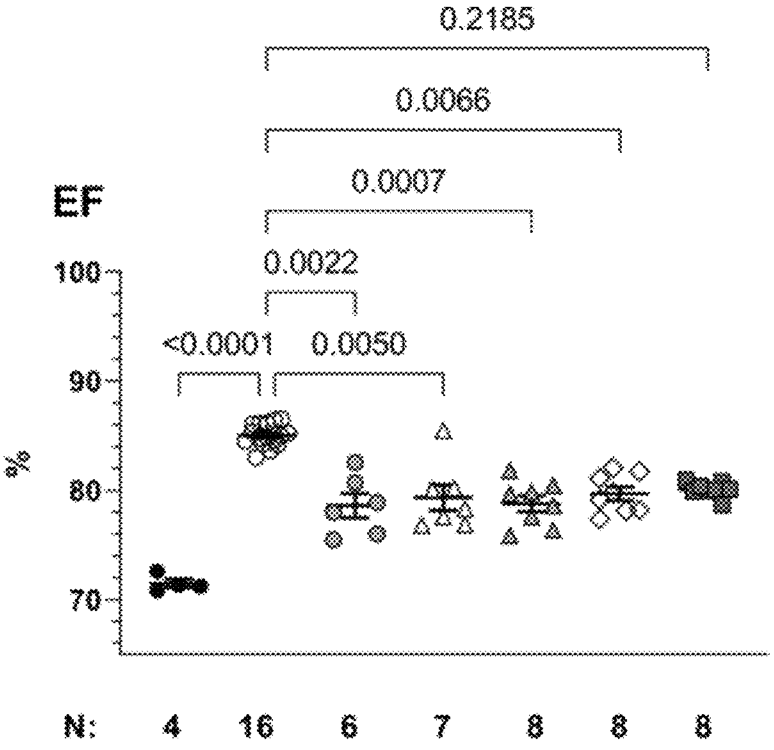
Figure 15:
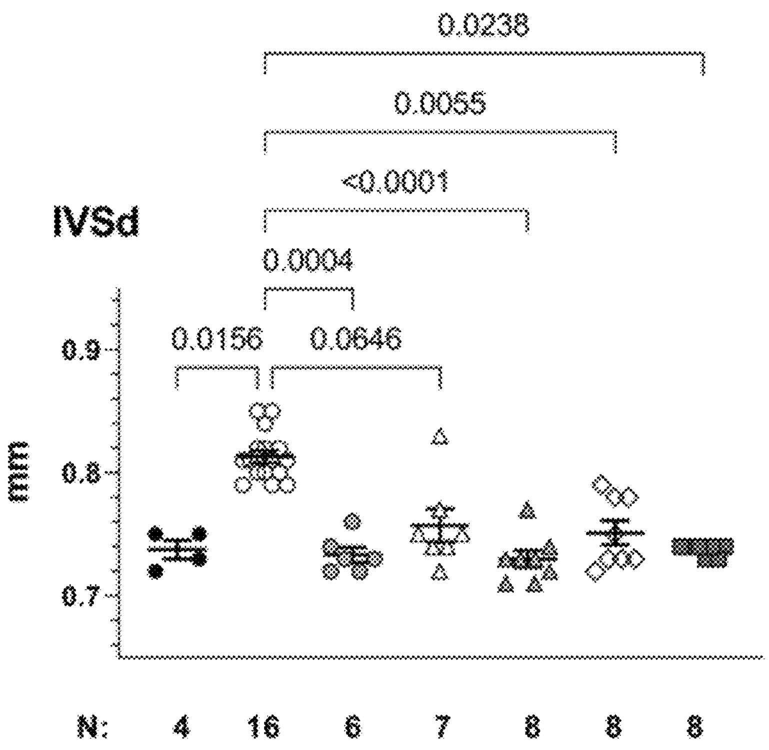
Figure 15:
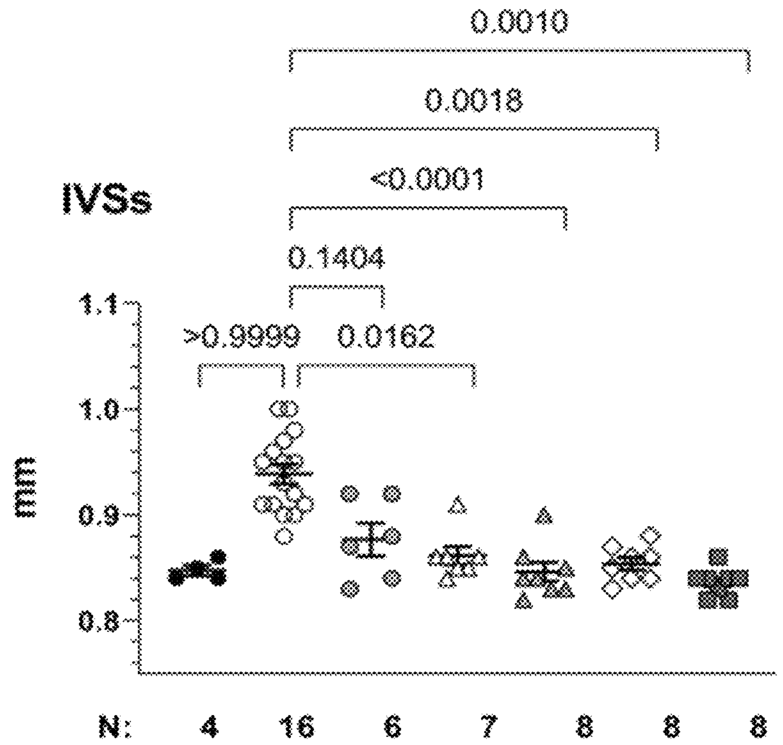
Figure 15:
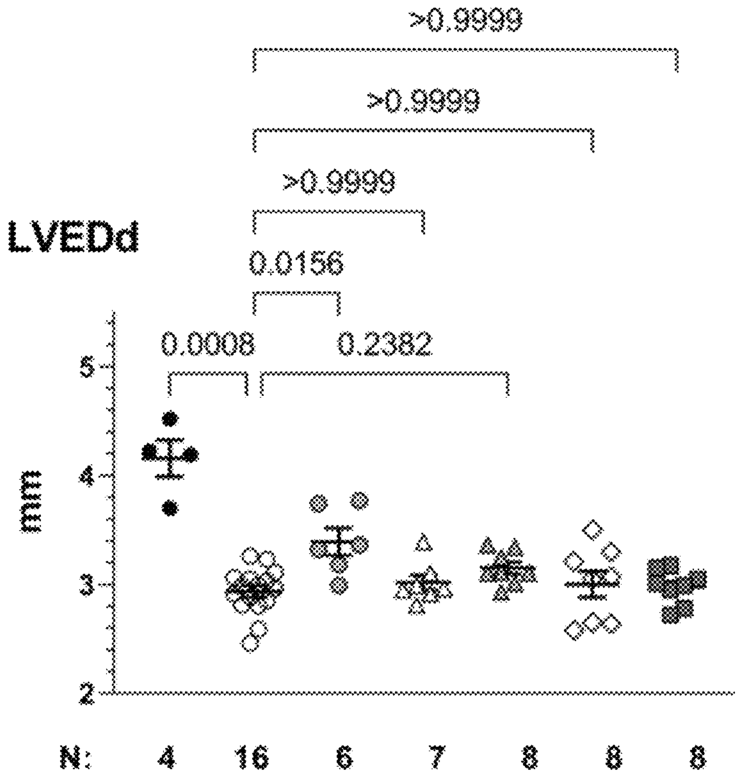
Figure 15:
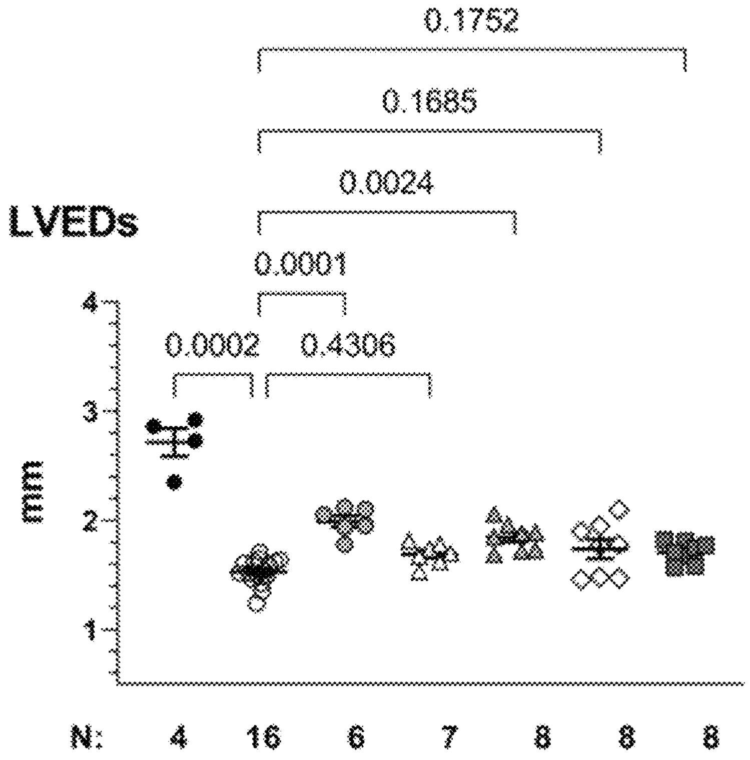
Figure 15:
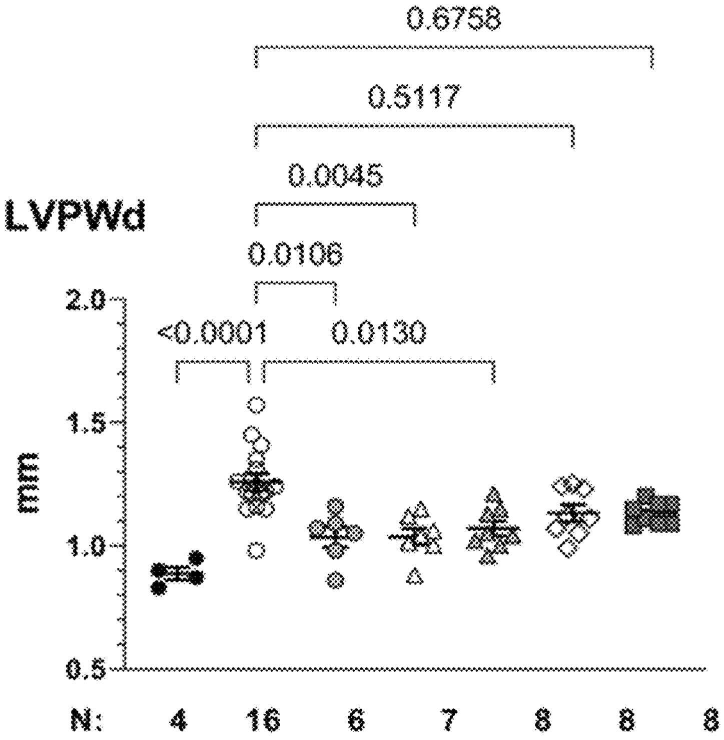
Figure 15:
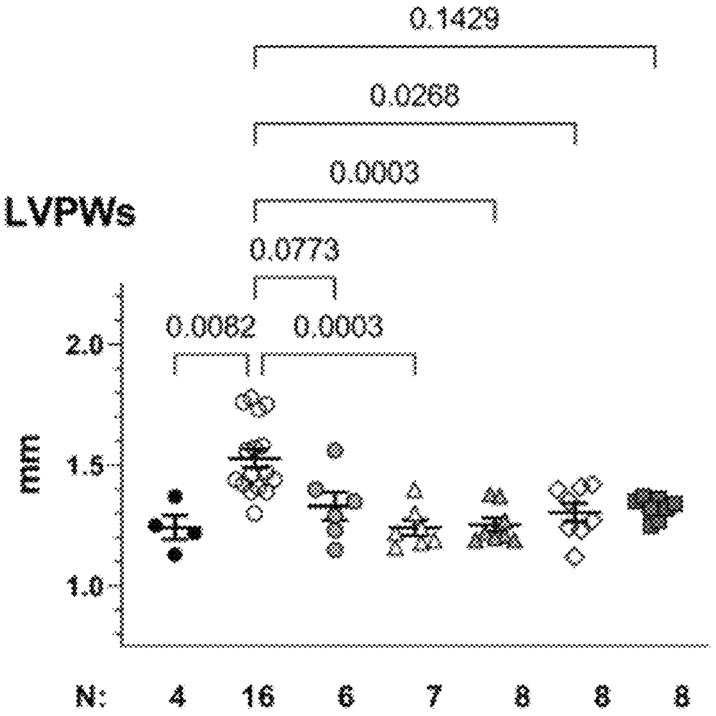
Figure 15:
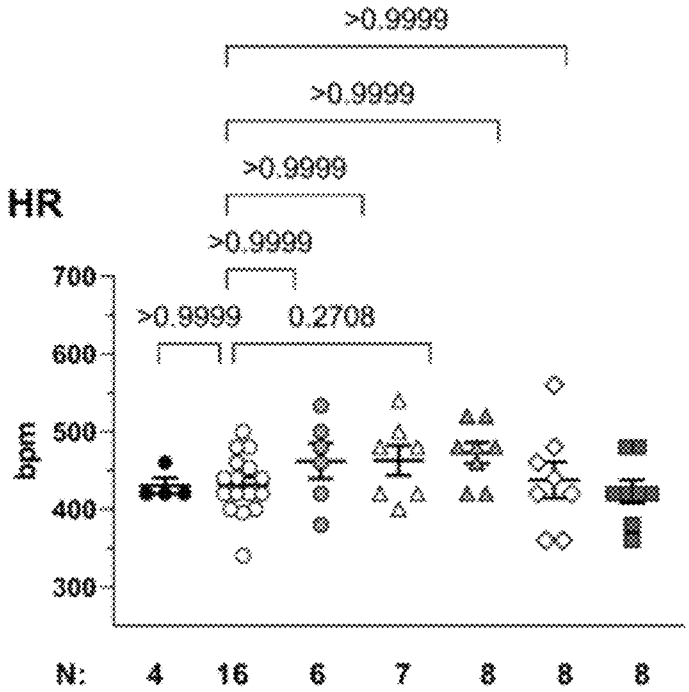
Figure 15:
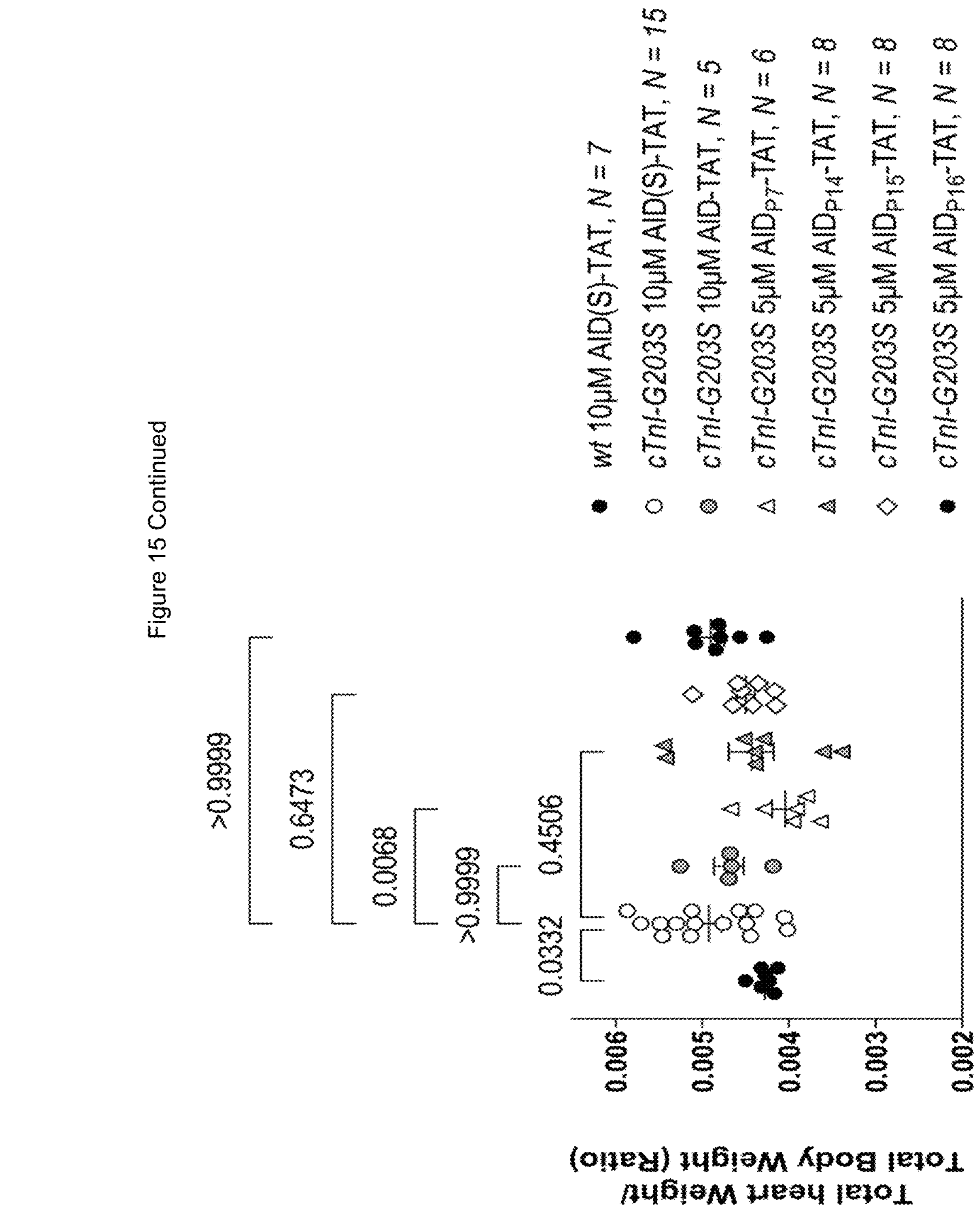

Echocardiographic assessment of cTnI-G203S mice reveal the development of HCM characteristics from approximately 21 weeks of age (Viola H, Johnstone V, Cserne Szappanos H, Richman T, Tsoutsman T, Filipovska A, et al. The L-type Ca (2+) channel facilitates abnormal metabolic activity in the cTnI-G203S mouse model of hypertrophic cardiomyopathy. *J Physiol.* 2016; 594 (14): 4051-70; Viola H M, Shah A A, Johnstone V P A, Cserne Szappanos H, Hodson M P, Hool L C. Characterization and validation of a preventative therapy for hypertrophic cardiomyopathy in a murine model of the disease. *Proc Natl Acad Sci USA.* 2020; 117 (37): 23113-24). Consistent with previous findings, 20-week-old cTnI-G203S mice treated with 10 μM AID(S)-TAT until 25-weeks of age (10 μM, 3×/wk/5 wk) (peptide was dissolved in phosphate buffered saline solution (PBS), and the total amount of the 10 μM AID-TAT mutant peptides administered over 5 weeks was 0.9 mg), developed a significant decrease in left-ventricular end diameter (LVEDd and LVEDs), and a significant increase in fractional shortening (FS), ejection fraction (EF), left-ventricular posterior wall thickness (LVPWd and LVPWs) and interventricular septum (IVDs), compared to wt age-matched mice treated with AID(S)-TAT (FIG. 15). Additionally, age-matched cTnI-G203S mice treated with 10 μM AID-TAT demonstrated restored FS, EF, IVSd, LVEDd, LVEDs and LVPWd versus AID(S)-TAT treated cTnI-G203S mice (FIG. 15). FIG. 15 presents: LVEDd, left ventricular end diameter during diastole; LVEDs, left ventricular end diameter during systole; FS, fractional shortening; EF, ejection fraction; LVPWd, left ventricular posterior wall in diastole; LVPWs, left ventricular posterior wall in systole; IVDd, intraventricular septum in diastole; IVDs, intraventricular septum in systole; HR, heart rate. N=number of mice. Values reported as mean±SEM; P values compared with cTnI-G203S AID(S)-TAT as determined by the Kruskal-Wallis test.

The efficacy of treating 20-week-old pre-hypertrophic cTnI-G203S mice with 5 μM AID-TAT variants was examined using the same treatment protocol (3×/wk/5 wk). We performed echocardiography on mice before and after the 5-week treatment to assess cardiac morphology and function. Treatment of cTnI-G203S mice with 5 μM $AID_{P7}$-TAT (P7-TAT) effectively restored FS, EF, IVSs, LVPWd and LVPWs versus AID(S)-TAT, in a similar manner to 10 μM AID-TAT (FIG. 15). A trend toward increased LVEDd and LVEDs, and decreased IVDS was observed (FIG. 15). Interestingly, 25-week-old cTnI-G203S mice treated with 5 μM $AID_{P7}$-TAT (SEQ ID 4-TAT) demonstrate a significant decrease in LVPWs and IVSs that was not achieved with 10 μM AID-TAT (FIG. 15). Treatment of cTnI-G203S mice with 5 μM $AID_{P14}$-TAT (P14-TAT) effectively restored all echocardiographic parameters (except LVEDd). This included some that were not altered by 10 μM AID-TAT (FS, EF, IVSd, IVSs, LVEDs, LVPWd and LVPWs). A trend toward increased LVEDd was observed. In other cohorts, 5 μM $AID_{P15}$-TAT (P15-TAT) effectively restored FS, EF, IVSd, IVSs and LVPWs, while treatment with 5 μM AID$_{P16}$-TAT (P16-TAT) demonstrated restored IVSd and IVSs only.

The effect of treatment of the mice with peptides on the development of hypertrophy assessed as changes in heart weight to body weight ratio was also examined. We found that treatment with 5 μM AID$_{P7}$-TAT (P7-TAT) or 5 μM AID$_{P14}$-TAT (P14-TAT) significantly decreased heart weight/body weight indicating a regression in the hypertrophy (FIG. 16). FIG. 16 presents the mean±SEM of heart weight to body weight ratio measurements from wt and cTnI-G203S mice treated with 10 μM AID(S)-TAT, 10 μM AID-TAT, 5 μM AID$_{P7}$-TAT, 5 μM AID$_{P14}$-TAT, 5 μM AID$_{P15}$-TAT or 5 μM AID$_{P16}$-TAT. n=number of mice as indicated. *$P<0.05$, **$P<0.01$ compared with cTnI-G203S AID(S)-TAT as determined by Kruskal-Wallis tests.

Overall, this data indicates that treatment prior to the development of hypertrophy with the peptides of the invention prevents the development of hypertrophy, regresses fibrosis and improves cardiac function in cTnI-G203S mice. The variant peptides are more efficacious than the original AID-TAT in the prevention of hypertrophy.

The invention claimed is:

1. A peptide comprising the amino acid sequence:

QQX1EEDX2KGYLDWITQAE wherein X1 is an amino acid selected from the group comprising: Q, E or R; and wherein X2 is an amino acid selected from the group comprising: L or E;

or a variant thereof, wherein the peptide does not consist of SEQ ID NO: 1.

2. A method for treating or reducing myocardial damage in a subject, comprising administering to the subject a peptide according to claim 1.

3. A polynucleotide encoding a peptide according to claim 1.

4. A pharmaceutical, prophylactic or therapeutic composition comprising: a peptide of claim 1, and one or more pharmaceutically acceptably carriers and/or diluents.

5. A kit to treat, prevent or ameliorate the effects of myocardial damage and/or oxidative stress in the heart of a subject, wherein the kit comprises at least a peptide according to claim 1, packaged in a suitable container, together with instructions for its use.

6. A peptide comprising any one of the amino acid sequences of SEQ ID NO: 4-7, wherein the peptide does not consist of SEQ ID NO: 1.

* * * * *

SEQUENCE LISTING

<160> NUMBER OF SEQ ID NOS: 17

<210> SEQ ID NO 1
<211> LENGTH: 18
<212> TYPE: PRT
<213> ORGANISM: Unknown
<220> FEATURE:
<223> OTHER INFORMATION: AID Peptide

<400> SEQUENCE: 1

Gln Gln Leu Glu Glu Asp Leu Lys Gly Tyr Leu Asp Trp Ile Thr Gln
1 5 10 15

Ala Glu

<210> SEQ ID NO 2
<211> LENGTH: 18
<212> TYPE: PRT
<213> ORGANISM: Unknown
<220> FEATURE:
<223> OTHER INFORMATION: Variant AID Peptide
<220> FEATURE:
<221> NAME/KEY: misc_feature
<222> LOCATION: (3)..(3)
<223> OTHER INFORMATION: Xaa is a Gln, Glu, or Arg
<220> FEATURE:
<221> NAME/KEY: misc_feature
<222> LOCATION: (6)..(6)
<223> OTHER INFORMATION: Xaa is Leu or Glu

<400> SEQUENCE: 2

Gln Gln Xaa Glu Glu Xaa Leu Lys Gly Tyr Leu Asp Trp Ile Thr Gln
1 5 10 15

Ala Glu

<210> SEQ ID NO 3
<211> LENGTH: 10
<212> TYPE: PRT
<213> ORGANISM: Unknown
<220> FEATURE:
<223> OTHER INFORMATION: TAT Peptide
<220> FEATURE:
<221> NAME/KEY: misc_feature
<222> LOCATION: (10)..(10)
<223> OTHER INFORMATION: Xaa is a 6-amino hexanoic acid

<400> SEQUENCE: 3

Arg Lys Lys Arg Arg Gln Arg Arg Arg Xaa
1 5 10

<210> SEQ ID NO 4
<211> LENGTH: 18
<212> TYPE: PRT
<213> ORGANISM: Unknown
<220> FEATURE:
<223> OTHER INFORMATION: Variant P7

<400> SEQUENCE: 4

Gln Gln Gln Glu Glu Asp Leu Lys Gly Tyr Leu Asp Trp Ile Thr Gln
1 5 10 15

Ala Glu

<210> SEQ ID NO 5
<211> LENGTH: 18
<212> TYPE: PRT
<213> ORGANISM: Unknown
<220> FEATURE:
<223> OTHER INFORMATION: Varian P14

<400> SEQUENCE: 5

Gln Gln Glu Glu Glu Asp Leu Lys Gly Tyr Leu Asp Trp Ile Thr Gln
1 5 10 15

Ala Glu

<210> SEQ ID NO 6
<211> LENGTH: 18
<212> TYPE: PRT
<213> ORGANISM: Unknown
<220> FEATURE:
<223> OTHER INFORMATION: Variant P15

<400> SEQUENCE: 6

Gln Gln Glu Glu Glu Asp Glu Lys Gly Tyr Leu Asp Trp Ile Thr Gln
1 5 10 15

Ala Glu

<210> SEQ ID NO 7
<211> LENGTH: 18
<212> TYPE: PRT
<213> ORGANISM: Unknown
<220> FEATURE:
<223> OTHER INFORMATION: Variant P16

<400> SEQUENCE: 7

Gln Gln Arg Glu Glu Asp Leu Lys Gly Tyr Leu Asp Trp Ile Thr Gln
1 5 10 15

Ala Glu

<210> SEQ ID NO 8
<211> LENGTH: 5
<212> TYPE: PRT
<213> ORGANISM: Unknown
<220> FEATURE:
<223> OTHER INFORMATION: Nuclear Localisation Signal

<400> SEQUENCE: 8

Gly Arg Lys Lys Arg
1 5

<210> SEQ ID NO 9
<211> LENGTH: 11
<212> TYPE: PRT
<213> ORGANISM: Unknown
<220> FEATURE:
<223> OTHER INFORMATION: Protein transduction domain

<400> SEQUENCE: 9

Tyr Gly Arg Lys Lys Arg Arg Gln Arg Arg Arg
1 5 10

-continued

```
<210> SEQ ID NO 10
<211> LENGTH: 18
<212> TYPE: PRT
<213> ORGANISM: Unknown
<220> FEATURE:
<223> OTHER INFORMATION: AID [S] Peptide

<400> SEQUENCE: 10

Gln Lys Ile Leu Gly Glu Trp Asp Leu Ala Gln Tyr Thr Asp Gln Glu
1               5                   10                  15

Leu Glu


<210> SEQ ID NO 11
<211> LENGTH: 13
<212> TYPE: PRT
<213> ORGANISM: Unknown
<220> FEATURE:
<223> OTHER INFORMATION: Variant P1

<400> SEQUENCE: 11

Asp Leu Lys Gly Tyr Leu Asp Trp Ile Thr Gln Ala Glu
1               5                   10


<210> SEQ ID NO 12
<211> LENGTH: 16
<212> TYPE: PRT
<213> ORGANISM: Unknown
<220> FEATURE:
<223> OTHER INFORMATION: Variant P4

<400> SEQUENCE: 12

Leu Glu Glu Asp Leu Lys Gly Tyr Leu Asp Trp Ile Thr Gln Ala Glu
1               5                   10                  15


<210> SEQ ID NO 13
<211> LENGTH: 11
<212> TYPE: PRT
<213> ORGANISM: Unknown
<220> FEATURE:
<223> OTHER INFORMATION: Variant P6

<400> SEQUENCE: 13

Lys Gly Tyr Leu Asp Trp Ile Thr Gln Ala Glu
1               5                   10


<210> SEQ ID NO 14
<211> LENGTH: 12
<212> TYPE: PRT
<213> ORGANISM: Unknown
<220> FEATURE:
<223> OTHER INFORMATION: Variant P10

<400> SEQUENCE: 14

Asp Leu Lys Gly Tyr Leu Asp Trp Ile Thr Gln Ala
1               5                   10


<210> SEQ ID NO 15
<211> LENGTH: 11
<212> TYPE: PRT
<213> ORGANISM: Unknown
<220> FEATURE:
<223> OTHER INFORMATION: Variant P11

<400> SEQUENCE: 15

Asp Leu Lys Gly Tyr Leu Asp Trp Ile Thr Gln
1               5                   10
```

-continued

```
<210> SEQ ID NO 16
<211> LENGTH: 10
<212> TYPE: PRT
<213> ORGANISM: Unknown
<220> FEATURE:
<223> OTHER INFORMATION: Variant P12

<400> SEQUENCE: 16

Asp Leu Lys Gly Tyr Leu Asp Trp Ile Thr
1               5                   10


<210> SEQ ID NO 17
<211> LENGTH: 18
<212> TYPE: PRT
<213> ORGANISM: Unknown
<220> FEATURE:
<223> OTHER INFORMATION: Variant P13

<400> SEQUENCE: 17

Gln Gln Leu Glu Glu Asp Leu Lys Gly Phe Leu Asp Ala Ala Thr Gln
1               5                   10                  15

Ala Glu
```